United States Patent [19]

Diehl et al.

[11] 4,240,822
[45] Dec. 23, 1980

[54] METHOD FOR CONTROLLING UNDESIRABLE PLANTS USING 1H-BENZOTRIAZOLE AND 2H-BENZOTRIAZOLE COMPOUNDS

[75] Inventors: Robert E. Diehl, Lawrenceville, N.J.; Roger V. Kendall, New Haven, Vt.

[73] Assignee: American Cyanamid Company, Stamford, Conn.

[21] Appl. No.: 965,763

[22] Filed: Dec. 4, 1978

Related U.S. Application Data

[63] Continuation of Ser. No. 760,601, Jan. 19, 1977, abandoned, which is a continuation-in-part of Ser. No. 645,064, Dec. 29, 1975, abandoned, which is a continuation of Ser. No. 490,422, Jul. 22, 1974, abandoned.

[51] Int. Cl.$^3$ ............................................. A01N 43/64
[52] U.S. Cl. ........................................ 71/92; 548/259
[58] Field of Search ............................................ 71/92

[56] References Cited

U.S. PATENT DOCUMENTS

| | | | |
|---|---|---|---|
| 2,927,883 | 3/1960 | Hosler et al. | 71/92 |
| 3,231,579 | 1/1966 | Pawloski | 71/92 |
| 3,255,194 | 6/1966 | Dill | 71/92 |
| 3,268,526 | 8/1966 | Newallis et al. | 71/92 |
| 3,301,832 | 1/1967 | D'Amico | 71/92 |
| 3,472,866 | 10/1969 | Newbold et al. | 71/92 |
| 3,592,822 | 7/1971 | Gilbert et al. | 71/92 |
| 3,637,736 | 1/1972 | Minieri | 71/92 |
| 3,652,580 | 3/1972 | Janiak et al. | 71/92 |
| 3,875,173 | 4/1975 | O'Doherty | 71/92 |
| 3,890,343 | 6/1975 | Miesel | 71/92 |

FOREIGN PATENT DOCUMENTS

990111  4/1965  United Kingdom ................. 424/269

OTHER PUBLICATIONS

Picci et al., "Effect of Benzotriazolylalkanoic acids, etc;" (1968) CA68, No. 77089x (1968).
Picci, "Effect of Benzotriazole and two, etc;" (1966) CA64, p. 14879 (1966).
Klingensmith, "Effect of certain Benzazole compds, etc;" (1961) CA55, p. 7568 (1961).
Brady et al., "Triazole Compounds. Part I. Some, etc;" (1923) J. Chem. Soc. 123, pp. 2258-2267 (1923).

*Primary Examiner*—Glennon H. Hollrah
*Attorney, Agent, or Firm*—Harry H. Kline

[57] ABSTRACT

The invention is a method for the control of undesirable broadleaf weeds and grass weeds. More particularly, the invention relates to a method for controlling undesirable weeds by applying to the foliage thereof or to soil containing seeds of the undesirable weeds, a herbicidally effective amount of a 1H-benzotriazole or 2H-benzotriazole compound.

15 Claims, No Drawings

METHOD FOR CONTROLLING UNDESIRABLE PLANTS USING 1H-BENZOTRIAZOLE AND 2H-BENZOTRIAZOLE COMPOUNDS

This application is a continuation of our co-pending application, Ser. No. 760,601, filed Jan. 19, 1977, now abandoned which in turn is a continuation-in-part of U.S. Ser. No. 645,064, filed Dec. 29, 1975, now abandoned, which in turn is a continuation of U.S. Ser. No. 490,422, filed July 22, 1974, now abandoned.

BACKGROUND OF THE INVENTION

1. Field of the Invention

The invention pertains to chemicals useful as herbicides.

2. Description of the Prior Art

The compound 4-nitro-1H-benzotriazole is within the generic disclosure of Japanese patent application showa No. 44-49635 dated June 23, 1969 (showa No. 44), applicant Nitto Chemical Industrial Company 1-5-1, Marunouchi, Chiyoda-Ku, Tokyo. The Japanese patent teaches the use as a soil additive which decreases nitrate formation rather than ammonia.

SUMMARY OF THE INVENTION

The invention is herbicidal use. More particularly the invention relates to a method for the control of undesirable plant species by applying to the foliage thereof or to soil containing seeds of the undesirable plant species, a herbicidally effective amount of a benzotriazole compound represented by the formula:

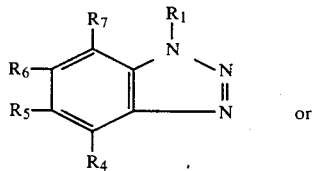
(I)

or

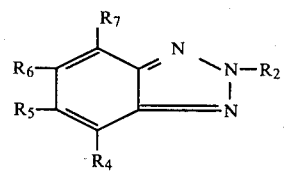
(II)

wherein $R_1$ and $R_2$ each independently represent hydrogen, alkyl $C_1$–$C_{10}$ (straight chain or branched and preferably secondary alkyl $C_3$–$C_7$), phenyl, acyl $C_2$–$C_5$ optionally substituted with from 1 to 3 halogen atoms, benzoyl, hydroxy, alkoxy $C_3$–$C_{10}$ (preferably $C_3$–$C_7$ branched), acyloxy $C_1$–$C_5$, dialkylcarbamoyl $C_1$–$C_5$ benzyl, cycloalkenyl $C_3$–$C_8$, —$(CH_2)_n$-cycloalkyl ($C_3$–$C_8$) optionally substituted with a hydroxy, alkoxy $C_1$–$C_3$, alkyl $C_1$–$C_3$ or

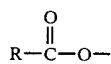

wherein R is hydrogen or $C_1$–$C_2$ alkyl and n is 0 or 1; cyclohexylone or

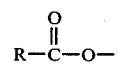

where n is 0 or 1; $R_4$, $R_5$, $R_6$ and $R_7$ each independently represent hydrogen, alkyl $C_1$–$C_4$ (preferably methyl), alkoxy $C_1$–$C_4$ (preferably methoxy) nitro, halogen (preferably chloro or bromo), halomethyl (mono, di or trihalo such as $CF_3$), methyl sulfonyl, carboxy, isothiocyano, or cyano, with the proviso that at least one of said $R_4$, $R_5$, $R_6$ and $R_7$ represents a member other than hydrogen.

DETAILED DESCRIPTION AND PREFERRED EMBODIMENTS

As used in this specification, the term "halogen" means fluorine, chlorine, bromine and iodine; however, chlorine and bromine are preferred.

While the above-identified compounds are effective pre-emergence and post-emergence herbicidal agents, preferred compounds and 1H-benzotriazoles and 2H-benzotriazoles represented by formulas I and II above, but, wherein $R_1$ and $R_2$ each independently represent secondary alkyl $C_3$–$C_7$; benzyl; cycloalkenyl $C_3$–$C_8$; —$(CH_2)_n$—cycloalkyl ($C_3$–$C_8$) optionally substituted with a hydroxy, alkoxy $C_1$–$C_3$, alkyl $C_1$–$C_3$, or

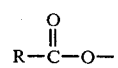

wherein R is hydrogen or $C_1$–$C_2$ alkyl and n is 0 or 1; cyclohexylone or

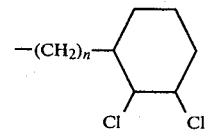

where n is 0 or 1; $R_4$ represents hydrogen, chloro, cyano, methoxy or nitro; $R_5$ and $R_6$ are both hydrogen or both methyl; $R_7$ is hydrogen or nitro; with the proviso that when $R_4$ is nitro, chloro, methoxy or cyano, then $R_5$, $R_6$ and $R_7$ are each hydrogen and when $R_4$ is hydrogen then $R_7$ is nitro and $R_5$ and $R_6$ are each methyl. Still more preferred are the 1H-benzotriazoles as herein defined, and especially preferred are those in which $R_1$ is sec-alkyl $C_3$–$C_7$; —$(CH_2)_n$-cycloalkyl ($C_3$–$C_8$) optionally substituted with hydroxy, alkoxy $C_1$–$C_3$, alkyl $C_1$–$C_3$, or wherein R is $C_1$–$C_2$ alkyl and n is 0 or 1; cyclohexylone or

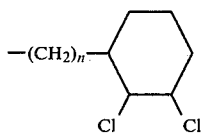

where n is 0 or 1.

Other preferred benzotrizoles are 1-H-benzotriazoles in which $R_1$ is alkoxy $C_3$-$C_4$, acetyl, chloroacetyl, 2-butanone, isobutyryl, t-butyl methoxymethylpropyl and $R_4$, $R_5$, $R_6$ and $R_7$ are as described above.

The compounds of this invention are highly effective herbicidal agents. Moreover, they are effective for the control of a wide variety of undesirable broadleaf weeds and grasses and may be used for either the pre-emergence or postemergence control of undesirable plants. In practice it is generally found that about 0.25 to 10.0 pounds per acre of the active compound, applied to the foliage of undesirable plants or to soil containing seeds of undesirable plants, provides excellent control of the plants. It is also found that such control can be achieved with both solid and liquid formulations containing the active compound; and further, that many of the compounds, particularly the preferred compounds, are highly selective and can be used for the control of undesirable plant species in the presence of crops such as corn, cotton, soybeans and rice.

The compounds of this invention can be formulated as dusts, wettable powders, granulars and flowables.

A dust formulation can be prepared by grinding the toxicant with a suitable inert diluent such as clay (attapulgite, Kaolin, etc.), diatomaceous earth, talc, or any other finely ground nonreactive organic or inorganic diluent. The potency of the dust may vary by 1 to 99%, depending upon the desired use for the product.

A wettable powder formulation can be prepared by blending the toxicant with an inert diluent (clay, talc, corn cob, etc.) dispersing agent (lignin sulfonate or neutral sodium salts of condensed aryl sulfonic acids), and if necessary, a wetting agent such as alkyl aryl polyethylene glycols of the dioctyl ester of sodium sulfosuccinic acid. The blended material is then ground in a suitable attrition mill until the desired particle size range is achieved. The usual concentration of a wettable powder is 50 to 80% toxicant, but higher or lower concentrations may be prepared. The dispersing agent is usually employed at the 5% level and the wetting agent from 1 to 2%. The inert diluent is used to make up the balance to 100%.

Flowable preparations of the herbicides can be prepared by grinding the toxicant, dispersing agent, wetting agent, inert diluent, in a solvent, e.g. water. The grinding is done by using a suitable attrition mill such as a ball mill or colloid mill.

The inert diluent, as well as the dispersing and wetting agents may be the same as those used in the wettable powder. A thickening agent, organic (hydroxymethyl cellulose) or inorganic (bentonite), may be used to increase the viscosity of the liquid. The potency of the flowable can vary from 10 to 70% with 50% being a reasonable concentration.

Granular preparation of the benzotriazoles can be prepared by impregnation. In impregnation, the compound is dissolved in a suitable solvent, volatile or nonvolatile, e.g., methylene chloride, acetone or a heavy aromatic solvent such as PANASOL®AN -2 or the like and the solution sprayed onto the clay. If it is desired, a wetting agent such as an alkyl aryl polyethylene glycol may be added to the spray solution. The solvent is then removed or allowed to remain on and thus prepared granular product. The concentration of the active agent on the granular carrier may range from 1 to 30% w/w with 3% being a practical level.

The compounds of the invention may be prepared by several different methods. The procedure employed depends upon the substituents present in the benzotriazole ring and also upon whether the benzotriazole is a 1H-benzotriazole or a 2H-benzotriazole.

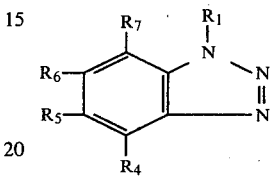

1H-Benzotriazole

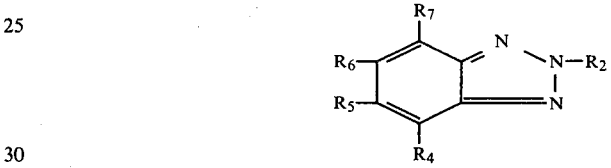

2H-Benzotriazole

The 1-alkyl-1H- and 2-alkyl-2H-benzotriazoles of the present invention may be prepared by the alkylation of the appropriate benzotriazole, either substituted or unsubstituted in the benzene ring, with an appropriate alkylating agent. The alkylating agent may be selected from the appropriate secondary or cyclic saturated or unsaturated aliphatic alkyl bromides and iodides containing from 3 to 8 carbons atoms. The reaction may be carried out by heating a mixture of the benzotriazole, a strong base such as an alkali metal hydroxide or alkali metal alkoxide, the alkylating agent and an organic solvent such as acetonitrile, dimethylformamide, dimethoxyethane, dimethyl sulfoxide, nitromethane or a lower alkyl $C_1$-$C_4$ ketone at a temperature of generally between 50° C. and 100° C.

The reaction for 1-alkyl-4-nitrobenzotriazole is illustrated below.

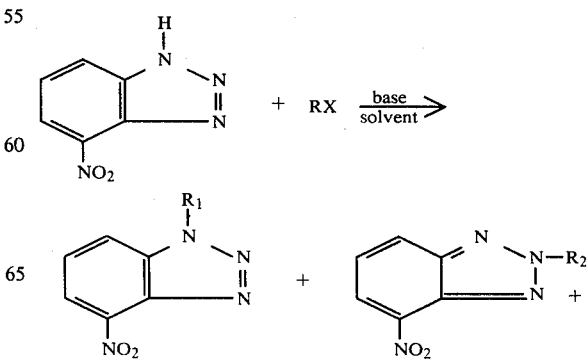

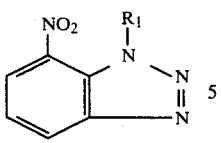

The 1-alkyl-1H-benzotriazoles can be separated from the 2-alkyl-2H-benzotriazole by an extraction with concentrated hydrochloric acid, or hydrobromic acid. The 2H-benzotriazoles are insoluble in the acid whereas the 1H-benzotriazoles are soluble. Separation of the 1-alkyl-4-nitro isomer and 1-alkyl-7-nitro isomer can be accomplished by fractional recrystallization or chromatography.

The 4-nitrobenzotriazoles can be prepared by nitration of the parent benzotriazole in a 90% nitric —23% oleum medium. The reaction is usually conducted at a temperature below 50° C. with excellent product yields being obtained.

The 1H-benzotriazoles may also be prepared by a three step synthesis from the appropriate 1-chloro-2-nitrobenzene.

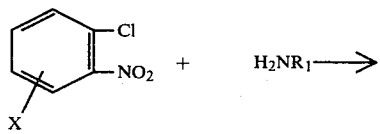

X = H, NO$_2$, alkyl etc.

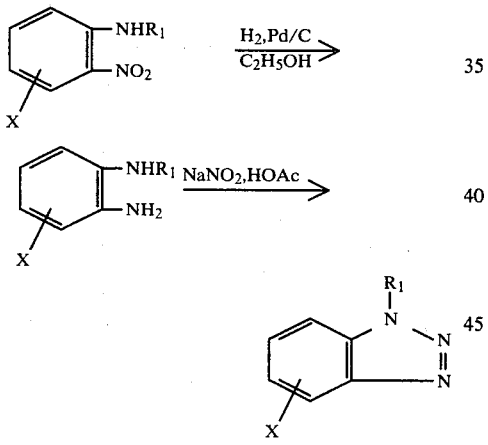

The first step is conveniently carried out by refluxing 1 part of the 1-chloro-2-nitrobenzene with three parts of a primary amine (C$_3$ to C$_8$, branched or cylic aliphatic chains) for several hours to several days depending on the amine. The reduction of the nitro group in the second step is readily accomplished via a catalytic hydrogenation with hydrogen and 10% palladium or platinum on carbon in a C$_1$–C$_4$ alcoholic solution. The third step may be carried out in dilute hydrochloric acid, acetic acid or carboxylic acid solution by adding an aqueous solution of sodium or potassium nitrite to an acetic or other carboxylic acid solution of the phenylenediamine. This reaction is generally carried out at about 25° C. to 30° C.

A third procedure involves the nitration of the 1H-alkylbenzotriazoles in a 90% nitric acid-23% oleum medium (1:2 ratio) which yields all four possible nitration products. The major product of the reaction is the 1-alkyl-4-nitro-benzotriazole. The nitration is generally carried out at a temperature of about 25° C. and is graphically illustrated as follows:

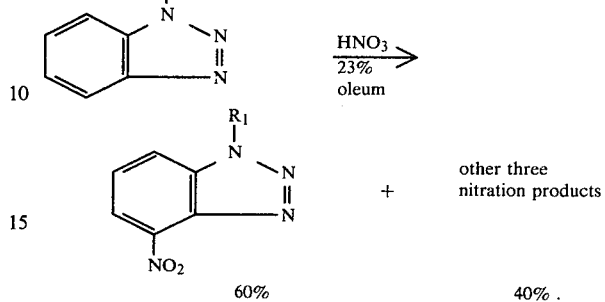

Benzotriazoles substituted in the benzene ring can also be nitrated by this procedure.

Nitration of the 2H-benzotriazoles can not be accomplished in the nitric acid-oleum medium since the sulfuric acid promotes the cleavage of the alkyl group. An exception is the 2-methylbenzotriazoles which are stable to the sulfuric acid. The nitration can be accomplished, however, with a 90% nitric acid-acetic anhydride medium which yields a 60:40 mixture of the two possible nitration products. This reaction is also generally conducted at a temperature below 25° C. and preferably between about 10° C. and 15° C. The reaction is graphically illustrated as follows:

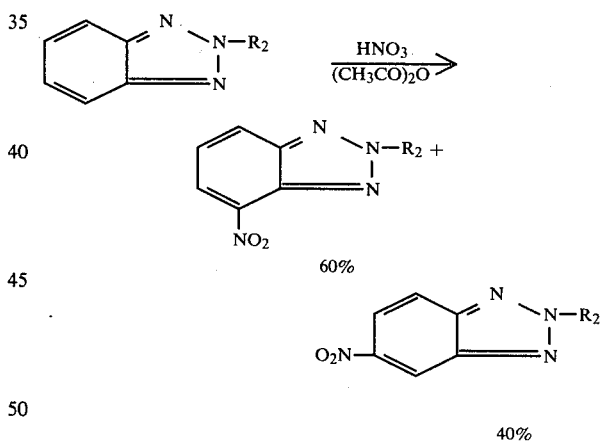

It has been found that the 2-alkyl-5,6-dimethylbenzotriazoles may be dinitrated with 90% nitric acid at 25° to 100° C. and preferably at about 50° C.

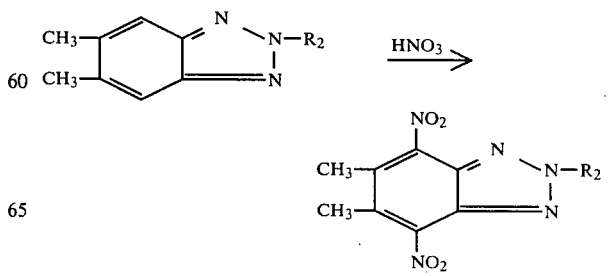

4-Nitrobenzotriazole may be conveniently acylated by a number of acylating agents. The reaction may be carried out by heating the 4-nitrobenzotriazole, preferably under relux conditions with an appropriate acylating agent such as the anhydrides of aliphatic acid, e.g. acetic anhydride, isobutyric anhydride and valeric anhydride, or with the correponding acyl $C_3$-$C_{10}$ halides.

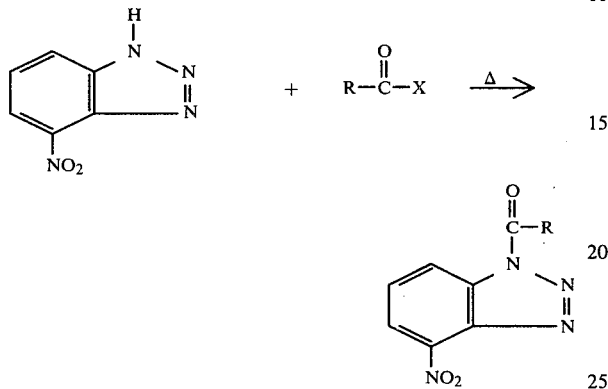

Only one product is isolated from the acylation reaction. It is not known for certain whether the acyl group is on the one or three position, but spectral data and steric considerations seems to support the 1-acyl-4-nitro configuration. In addition, 4-nitrobenzotriazole can be acylated with lower alkyl haloformates ($C_1$ to $C_6$) and with dialkycarbamoyl chlorides, e.g., dimethyl and diethyl. In these cases, the reaction is best carried out in a refluxing inert solvent such as benzene, toluene, glyme, xylene, ketones $C_1$-$C_6$, chlorinated hydrocarbons, and in the presence of a base such as triethylamine which neutralizes the hydrochloric acid which is generated.

The reaction of an appropriate dinitrochlorobenzene, such as 2,4-dinitrochlorobenzene and 2,6-dinitrochlorobenzene, with hydrazine hydrate in refluxing ethanol yields the corresponding 1-hydroxynitrobenzotriazole in high yield. The reaction is shown below.

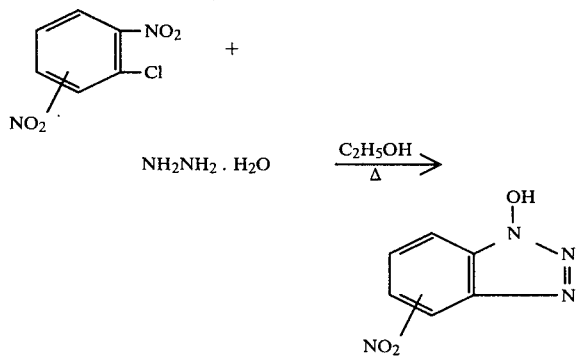

The sodium, potassium or some other convenient salt of 1-hydroxy-4 (or 6) nitrobenzotriazole can be readily alkylated with an appropriate ($C_1$-$C_8$) alkyl halide, such as ethyl, isopropyl, 3-pentyl or cyclohexyl bromide. The alkylation is best carried out in dimethylformamide.

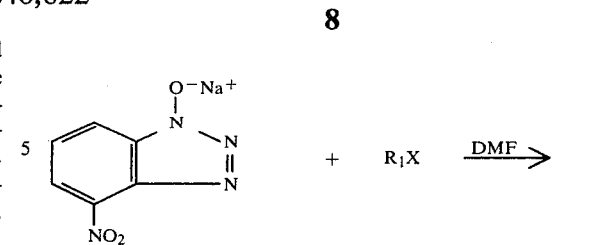

In a similar manner, the sodium salt of 1-hydroxybenzotriazole can be acylated with an appropriate acyl chloride ($C_1$-$C_6$) or with a dialkylcarbamoyl chloride.

EXAMPLE 1

Preparation of 1-sec-Butyl - 1H-benzotriazole and 2-sec-Butyl-2H-benzotriazole

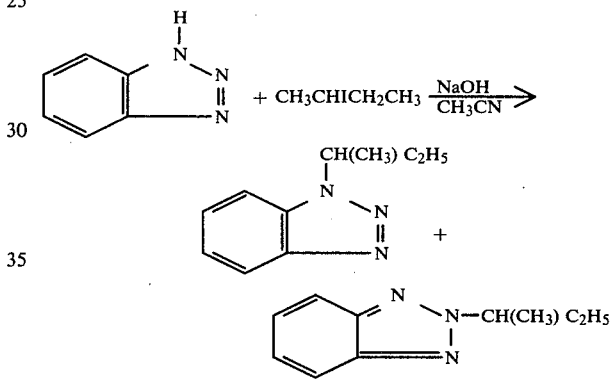

To a stirred solution of 96.0 grams of benzotriazole in 800 milliliters of acetonitrile at 50° C. is added 33.6 grams of sodium hydroxide pels. After most of the sodium hydroxide has reacted with the benzotriazole, 190 grams of 2-iodobutane is added in one portion and the resulting solution is refluxed for 15 hours. The acetonitrile is then evaporated and 300 milliliters of concentrated hydrochloric acid is added to the residual oil followed by the addition of 800 milliliters of benzene. The precipitated sodium iodide is removed by filtration. The acid layer is separated from the benzene layer and then washed three more times with 300 milliliters of benzene. The benzene washings are combined, dried over $MgSO_4$ and evaporated to yield 48 grams (34%) of the 2-sec-butyl-2H-benzotriazole as an oil. The material is purified by distillation, b.p. 0.25 mm Hg=63° C.

Analysis Calculated for $C_{10}H_{13}N_3$: C, 68.54; H, 7.48; N, 23.98. Found: C, 68.90; H, 7.62; N, 24.19.

To isolate the 1-sec-butyl isomer the concentrated hydrochloric acid layer is added to 1200 milliliters of ice water. The product oils out and then is extracted with chloroform. The chloroform extract is dried over $MgSO_4$ and evaporated to yield 69 grams (50%) of the 1-sec-butylbenzotriazole as an oil. The product is purified by distillation, b.p. 1.0 mm Hg=145°-149° C.

Analysis Calculated for $C_{10}H_{13}N_3$: C, 68.54; H, 7.48; N, 23.98. Found: C, 68.71; H, 7.51; N, 24.15.

Slightly higher yields of the two products are obtained when the alkyl bromide is used in place of the alkyl iodide.

EXAMPLE 2

Preparation of N-(1-Ethylpropyl)-o-nitroaniline

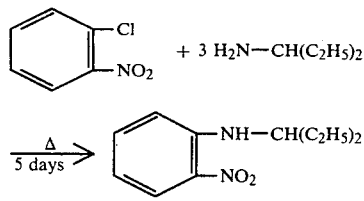

A solution of 158 grams of o-nitrochlorobenzene and 260 grams of 1-ethylpropylamine are refluxed together for 5 days. The solution is cooled and 500 ml. of water is added. Concentrated hydrochloric acid (10 milliliters) is added and the product separates out as an oil. The product is extracted with chloroform (2×200 milliliters), the extractions dried over MgSO4 and evaporated to yield 190 grams (91%) of product as an oil. The analytical sample is prepared by distillation of the crude oil, b.p. 1.8 mm Hg=148° C.

Analysis Calculated for $C_{11}H_{16}N_2O_2$: C, 63.44; H, 7.75; N, 13.45. Found: C, 63.16; H, 7.82; N, 13.16.

EXAMPLE 3

Preparation of N-(1-Ethylpropyl)-o-phenylenediamine

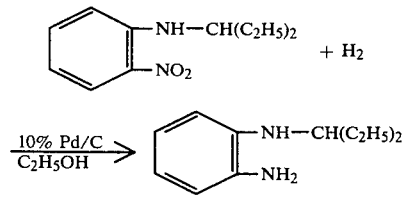

In a 2 liter Paar hydrogenator is placed 2.5 grams of 10% palladium on carbon catalyst, 800 milliliters of absolute alcohol and 250 grams of o-nitro-N-(1-ethylpropyl)aniline. Hydrogen is introduced and the reduction takes about 2½ hrs. The reaction is exothermic and the temperature subsides as the reaction goes to completion. The catalyst is removed by filtration and the ethanol evaporated to yield a nearly quantitative yield (214 grams) of product as a dark oil. A pure sample is obtained by vacuum distillation b.p. 2.0 mm Hg=125°-126° C.

EXAMPLE 4

Preparation of N-(1-Ethylpropyl) 1H-benzotriazole

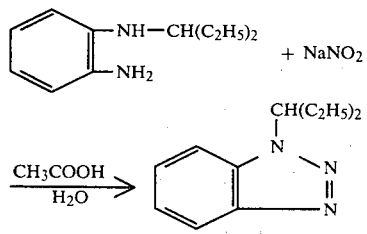

To a solution of the phenylenediamine (23.6 grams) in 120 milliliters of acetic acid cooled to 15° C. is slowly added 10.2 grams of NaNO2 in 50 milliliters of water. During the addition, the reaction temperature is not allowed to exceed 30° C. On completion of the addition, the reaction mixture is stirred an additional ½ hour at room temperature and then 50 milliliters of dichloroethane is added followed by 100 milliliters of water. The organic phase is separated, washed with a saturated sodium bicarbonate solution (50 milliliters) and then washed with 50 milliliters of water. The organic phase is dried over Na2SO4 and the solvent is evaporated to yield 15.8 grams (84%) of a dark liquid. The compound is purified by distillation, b.p. 1.7 mm Hg ca 139° C.

Analysis Calculated for $C_{11}H_{15}N_3$: C, 69.81; H, 7.99; N, 22.20. Found: C, 69.15; H, 8.14; N, 21.97.

EXAMPLE 5

Preparation of 1-(1-Ethylpropyl)-4-nitro 1H-benzotriazole

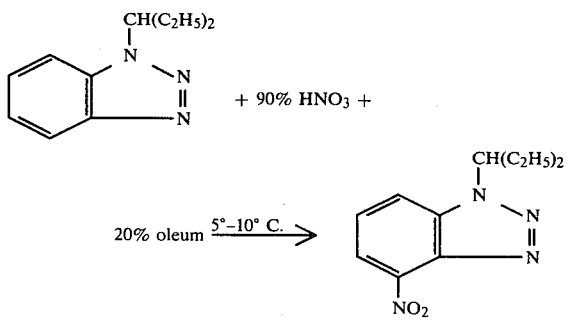

Over a 2½ hour period, 210 grams of the 1-(1-ethylpropyl)benzotriazole is added to a mixture of 100 milliliters of 90% nitric acid and 400 milliliters of 23% oleum with stirring. The mixed acid solution is cooled in an ice-salt bath and the addition rate is such that a temperature of between 5°-10° C. is maintained. The reaction mixture is maintained at 5°-10° C. for an additional 1½ hours and then at 25° C. for one more hour. The reaction mixture is then poured over 2500 grams of ice with stirring. After 15 minutes of stirring, the brown precipitate is collected by filtration, washed with additional water and air dried. The crude product is then slurried with 500 milliliters of 95% ethanol and then a second time with an additional 400 milliliter of hot 95% ethanol. The slurry is cooled and the product is collected by filtration and dried to yield 108.5 grams (45%) of brown solid, m.p. 129°-132° C. The analytical sample is recrystallized from chloroform-petroleum ether to give a m.p. 132°-134° C.

Analysis Calculated for $C_{11}H_{14}N_4O_2$: C, 56.40; H, 6.02; N, 23.92. Found: C, 56.38; H, 6.02; N, 24.27.

EXAMPLE 6

Preparation of 2-sec-Butyl-4-nitro-2H-benzotriazole and 2-sec-Butyl-5-nitro-2H-benzotriazole

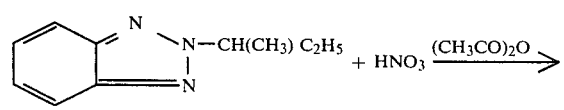

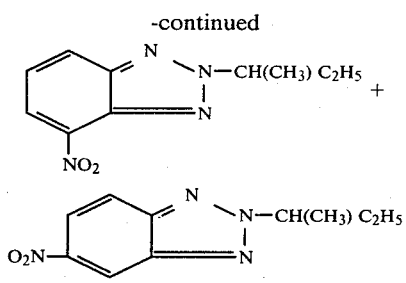

Over a period of 1 hour, 10.2 grams of 90% nitric acid is added to 5.0 grams 2-sec-butylbenzotriazole in 50 milliliters of acetic anhydride at 0° C. The reaction is then stirred at room temperature for an additional 3 hours. The reaction mixture is then poured over 200 grams of ice and water. Then 200 milliliters of chloroform is added and with stirring 10% sodium hydroxide is added to the two phase system until the aqueous layer is quite basic. The chloroform layer is dried over MgSO$_4$ and evaporated to yield 5.0 grams of an oil (mixture of the two nitration products). The two nitration products are separated by dry column, chromatography. Structure elucidation is based on comparison of their NMR spectra. The 4-nitro-2-sec-butylbenzotriazole is analyzed for $C_{10}H_{12}N_4O_2$: C, 54.33; H, 5.49; N, 25.44. Found: C, 54.30; H, 5.39; N, 25.44.

The 5-nitro-2-sec-butylbenzotriazole is analyzed for $C_{10}H_{12}N_4O_2$: C, 54.33; H, 5.49; N, 25.44. Found: C, 54.80; H, 5.69; N, 25.66.

EXAMPLE 7

Preparation of 1-(1-Ethylpropyl)-7-nitro-5-(trifluoromethyl)-1H-benzotriazole

Step 1

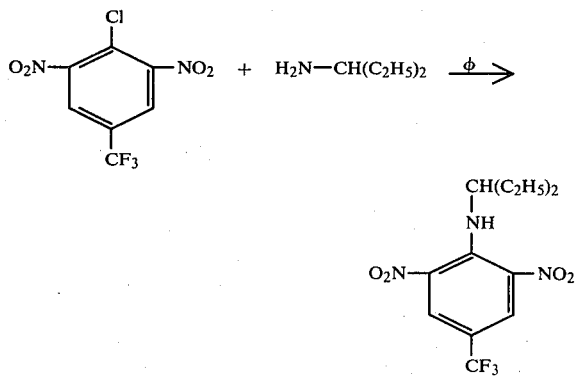

A solution consisting of 26 grams of 1-ethylpropylamine in 40 milliliters of benzene is slowly added in a dropwise fashion to a stirred solution of 40 grams of 4-chloro-3,5-dinitrobenzotrifluoride in 100 milliliters of the same solvent. The temperature of the mixture rises to 55°–60° C. and on completion of the addition, the reaction solution is stirred for an additional 2 hours. The hydrochloride salt of the amine is removed by filtration and the filtrate is then washed with brine, water and then finally dried over MgSO$_4$. The solvent is evaporated to yield 38.0 grams (80%), m.p. 71°–74° C.

Step 2

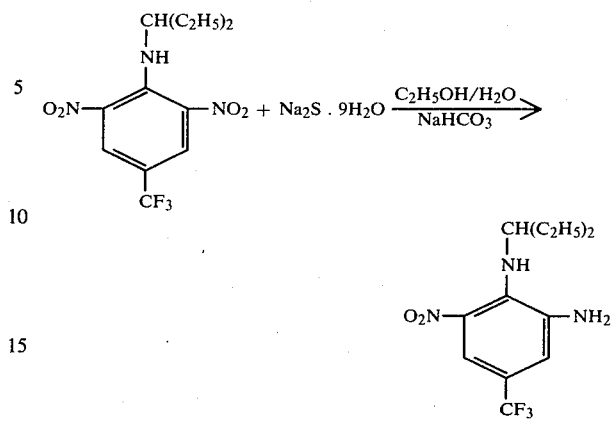

A solution consisting of 40 grams of sodium sulfide nonahydrate and 14 grams of sodium bicarbonate in 80 milliliters of water is slowly added to 16.8 grams of 3,5-dinitro-3-(1-ethylpropyl)aminobenzotrifluoride in 150 milliliters of absolute ethanol at such a rate as to maintain a temperature range of 50°–60° C. On completion of the addition, the reaction mixture is heated at 60° C. for 1 hour. Then 100 milliliters of water is added to the reaction mixture and the product is extracted with ethyl ether (3 × 150 milliliters). The solvent is dried over MgSO$_4$ and evaporated to yield the product as a dark red oil; 11.5 grams (78%). The crude product is used directly in the next step.

Step 3

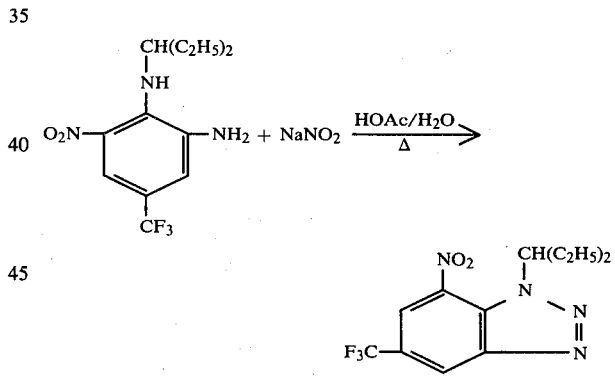

To a solution of 10.0 grams of the crude phenylenediamine in 30 milliliters of acetic acid and 15 milliliters of water is added in one portion 2.4 grams of sodium nitrite. After ½ hour an additional 2.4 grams of sodium nitrite is added to the reaction and the mixture is heated to 70° C. for 10 minutes. After cooling to room temperature, the reaction mixture is poured over ice and water and the crude product is extracted with ethyl ether (3 × 100 milliliters). The ether extracts are dried over MgSO$_4$ and the solvent evaporated to yield a dark oil. The product is purified by using dry column chromatography with chloroform being used as the eluting solvent. One gram (10%) of crude product is isolated, m.p. 42°–45° C. The crude product is recrystallized from n-hexane, m.p. 49.0°–49.5° C.

Analysis Calculated for $C_{12}H_{13}N_4O_2F_3$: C, 47.68; H, 4.33; N, 18.54. Found: C, 47.31; H, 4.26; N, 18.60.

EXAMPLE 8

Preparation of 4-Nitro 1H-benzotriazole

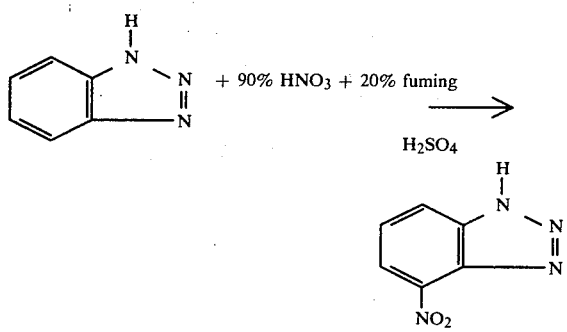

To a cooled solution (20° C.) of 1,060 milliliters of 20% fuming sulfuric acid and 265 milliliters of 90% nitric acid is added in a dropwise fashion a solution of 537 grams of benzotriazole in 1000 milliliters of concentrated sulfuric acid. The temperature is not allowed to exceed 50° C. At the end of the addition, the reaction mixture is allowed to stand at room temperature overnight. The reaction mixture is then poured over 9 liters of ice and water and a heavy yellow precipitate forms. The solid is collected by filtration, washed with water and dried. The solid, which is a mixture of the 4-nitro (90%) and the 5-nitro (10%) isomers, is then slurried with 7.5 liters of refluxing acetonitrile, the mixture cooled and 537 grams (73%) of pure 4-nitrobenzotriazole is collected by filtration, m.p. 228°–231° C.

EXAMPLE 9

Preparations of
5-Chloro-1-isopropyl-4-nitro-1H-benzotriazole and
5-Chloro-2-isopropyl-4-nitro-2H-benzotriazole

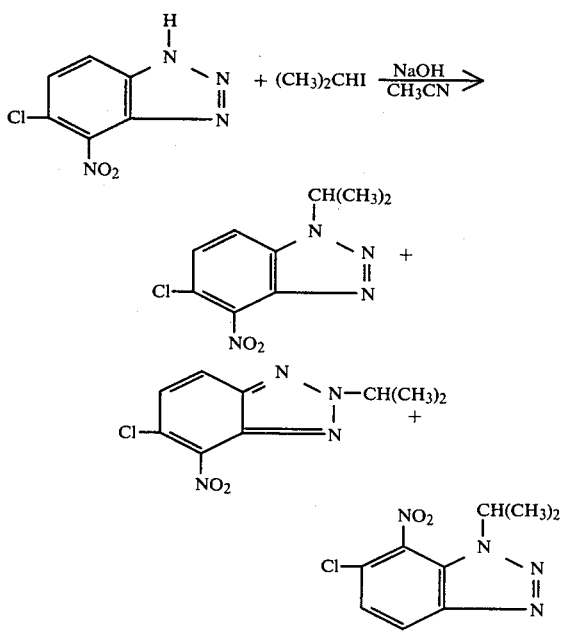

To a hot, stirred solution (50° C.) of 20.0 grams of 5-chloro-4-nitrobenzotriazole in 600 milliliters of acetonitrile is added 4.2 grams of sodium hydroxide pels and 20.0 grams of isopropyl iodide. The solution is then heated to reflux for 30 hours, filtered and the solvent removed by evaporation to yield an oil. The oil is extracted with concentrated hydrochloric acid (3×200 milliliters) and the resulting solid is collected, washed with water and air dried to yield 15.0 grams (63%) of crude 5-chloro-2-isopropyl 4-nitrobenzotriazole, m.p. 67°–70° C. The analytical sample is recrystallized from n-hexane and has a m.p. 75°–76° C.

Analysis Calculated for $C_9H_9N_4O_2CL$: C, 44.92; H, 3.77; N, 23.28. Found: C, 45.02, H, 3.69; N, 23.47.

To the acid filtrate is then added 1 liter of water and the aqueous mixture is extracted with ethyl ether (3×200 milliliters). The ethyl ether is dried over $MgSO_4$ and as the solvent is evaporated, the 5-chloro-1-isopropyl-4-nitrobenzotriazole crystallizes from solution. The product is collected by filtration to yield 3.1 grams (13%). The analytical sample is recrystallized from ethyl ether and has a m.p. of 130°–131° C.

Analysis Calculated for $C_9H_9N_4O_2Cl$: C, 44.92; H, 3.77; N, 23.28. Found: C, 45.06; H, 3.64; N, 23.53.

EXAMPLE 10

Preparation of 1-Isobutyryl-4-nitro-1H-benzotriazole

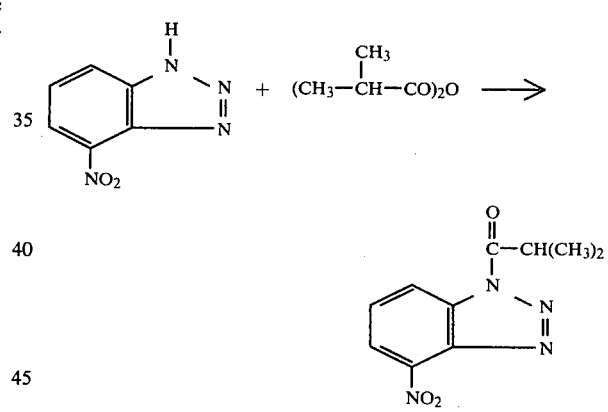

A solution of 4.0 grams of 4-nitrobenzotriazole in 20 milliliters of isobutyric anhydride are refluxed together for 2½ hours. The reaction mixture is poured over ice and the crude product is extracted with 200 milliliters of ethyl ether. The ether is dried and evaporated to yield an oily solid. The material is taken up in boiling cyclohexane (25 milliliters), treated with charcoal and filtered. On cooling, the product crystallizes from solution. The product is collected by filtration and dried to yield 3.2 grams (60%) of yellow-brown crystals, m.p. 114.5°–116° C. The analytical sample is recrystallized from methanol, m.p. 115°–116° C.

Analysis Calculated for $C_{10}H_{10}N_4O_3$: C, 51.28; H, 4.30; N, 23.92. Found: C, 51.23; H, 4.15; N, 24.25.

4-Nitrobenzotriazole can also be acylated using the corresponding acyl chloride derivative provided one uses triethylamine as an HCl scavenger.

EXAMPLE 11

Preparation of 1-Carboxylic acid,
4-nitro-1H-benzotriazole isobutyl ester

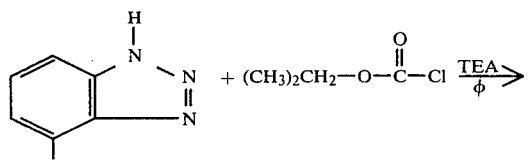

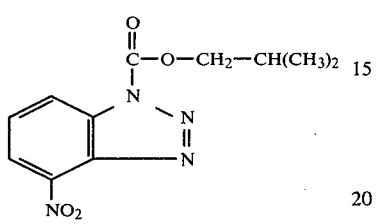

To a stirred slurry of 8.2 grams of 4-nitrobenzotriazole, 7 milliliters of triethylamine and 125 milliliters of benzene is slowly added 7 milliliters of isobutyl chloroformate. On completion of the addition, the mixture is heated to reflux for 30 minutes and then poured over ice. The product is extracted with ethyl ether and the ether is dried over MgSO$_4$ and evaporated to yield 10.2 grams (78%) of crude product. The analytical sample is recrystallized from carbon tetrachloride, m.p. 106.5°–107.5° C.

Analysis Calculated for $C_{11}H_{12}N_4O_2$: C, 50.00; H, 4.58; N, 21.20. Found: C, 50.12; H, 4.58; N, 21.49.

EXAMPLE 12

Preparation of 1-Carboxamide,
N,N-dimethyl-4-nitro-1H-benzotriazole and
1-Carboxamide,
N,N-dimethyl-7-nitro-1H-benzotriazole

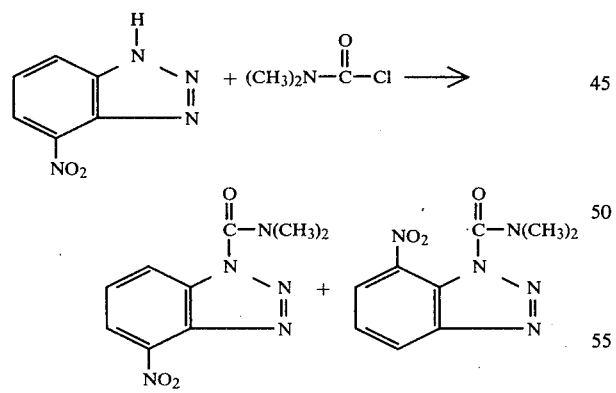

A mixture of 16.4 grams 4-nitrobenzotriazole, 14 milliliters of triethylamine, 11.5 grams of N,N-dimethyl carbamyl chloride and 250 milliliters of benzene is heated at reflux for 18 hours. The cooled reaction mixture is then poured into 1 liter of water and a solid precipitates from solution. The solid is collected, washed with water, ether and then dried to yield 17.7 grams (76%) of the 1-carboxamide 4-nitrobenzotriazole, 201°–203° C. The sample is recrystallized from benzene, m.p. 202°–203° C.

Analysis Calculated for $N_5O_3C_9H_9$: C, 45.96; H, 3.86; N, 29.78. Found: C, 45.91; H, 3.77; N, 29.83.

The benzene layer from the above filtrate is separated, dried over MgSO$_4$ and evaporated to yield 5.4 grams (23%) of the 1-carboxamide-7-nitrobenzotriazole, m.p. 114°–120° C. The material is recrystallized from methanol, m.p. 130°–130.5° C.

Analysis Calculated for $N_5O_3C_9H_9$: C, 45.96; H, 3.86; N, 29.78. Found: C, 45.81; H, 3.86; N, 30.00.

EXAMPLE 13

Preparation of 1-Hydroxy-4-nitro-1H-benzotriazole

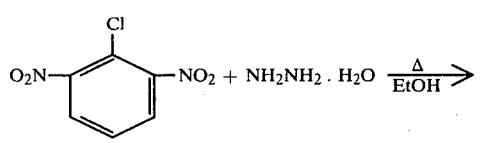

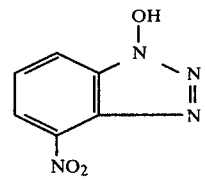

To a stirred hot solution of 60 grams of 2,4-dinitrochlorobenzene in 1 liter of absolute ethanol is slowly added 55 grams of hydrazine hydrate. A solid precipitates from solution as the hydrazine is added. After heating at the reflux temperature for 2 hours, the slurry is poured into 2 liters of water. The water-ethanol solution is filtered and the filtrate made acidic with concentrated hydrochloric acid. The product precipitates from the solution, is filtered, washed with water and air dried to give nearly a quantitative yield of product m.p. 225°–228° C. (dec.). The analytical sample is recrystallized from methanol, m.p. 231°–232° C.

Analysis Calculated for $C_6H_4N_4O_3$: C, 40.01; H, 2.38; N, 31.11. Found: C, 40.28; H, 2.38; N, 31.14.

The 1-hydroxy-6-nitrobenzotriazole is prepared by the same procedure except the starting material is 2,6-dinitrochlorobenzene.

EXAMPLE 14

Preparation of the acetate ester of
1-hydroxy-4-nitro-1H-benzotriazole

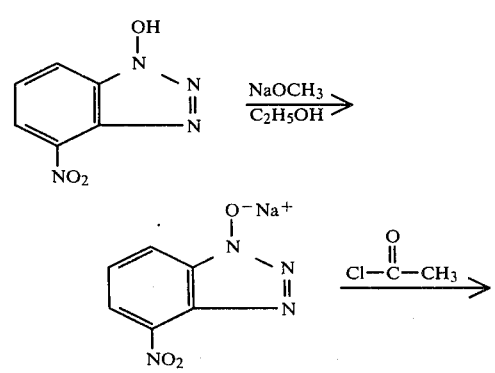

-continued

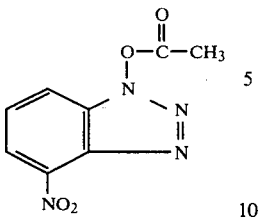

To a stirred hot solution of 31.4 grams of 1-hydroxy-4-nitrobenzotriazole in 1 liter of absolute ethanol is slowly added 10.8 grams of sodium methoxide. The sodium salt precipitates as a red solid and after ½ hour the salt is collected by filtration and dried, 33.4 grams (95%).

To a slurry of 8.0 grams of the sodium salt in 150 milliliters of acetone is added 4.5 grams of acetyl chloride. The red solid slowly dissolves and sodium chloride precipitates from solution. After ¼ hour, the sodium chloride is collected by filtration and the acetone filtrate evaporated to yield the crude product as a white solid, 5.0 grams (57%), m.p. 137°–139° C. The analytical sample is recrystallized from ethanol, m.p. 137°–138° C.

Analysis Calculated for $C_8H_6N_4O_4$: C, 43.25; H, 2.72; N, 25.22. Found: C, 43.16; H, 2.67; N, 25.41.

EXAMPLE 15

Preparation of 1-(1-Ethylproxy)-4-nitro-1H-benzotriazole

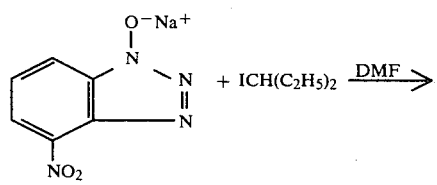

To a solution of 10.0 grams of the sodium salt of 1-hydroxy-4-nitrobenzotriazole in 200 milliliters of dry dimethylformamide is added 10.9 grams of 3-iodopentane and the mixture is allowed to stir at room temperature for 18 hours. The solution is then poured over 1500 milliliters of water and the product is extracted with ethyl ether (2×200 milliliters). Evaporation of the solvent yields an oil which crystallizes on standing, 7.9 grams (63%) of product, m.p. 61°–64° C. Recrystallization from ether: n-hexane (3:2) yields long colorless needles, m.p. 70°–72° C.

Analysis Calculated for $C_{11}H_{14}N_4O_3$: C, 52.79; H, 5.64; N, 22.39. Found: C, 52.68; H, 5.72; N, 22.64.

The sodium salt can be acylated by the same procedure by using a dialkyl carbamyl chloride.

EXAMPLE 16

Preparation of 4-nitro-2-phenyl-2H-benzotriazole

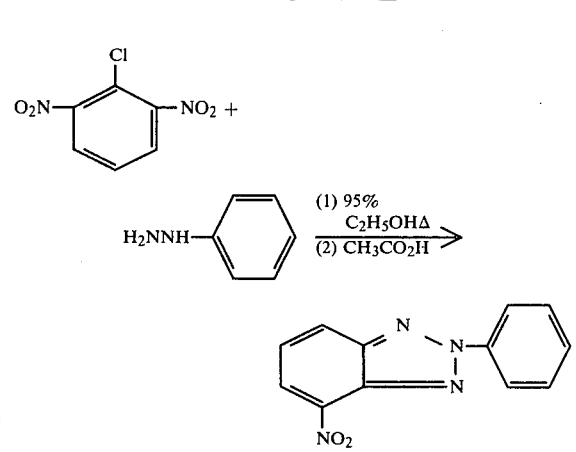

A solution of 40.6 grams of 2,6-dinitrochlorobenzene, 21.6 grams phenylhydrazine and 350 milliliters of 95% ethanol is heated at the reflux temperature for 22 hours. Then the solvent is evaporated to yield a dark oil. To the oil is added 70 milliliters of acetic acid and the mixture is heated to reflux for 6 hours. After cooling to room temperature, the crude product is collected by filtration, washed with petroleum ether and then washed with hot methanol to yield 8.5 grams (18%) of product m.p. 155°–156° C. The analytical sample is recrystallized from methanol, m.p. 155°–156° C.

Analysis Calculated for $C_{12}H_8N_4O_2$: C, 60.00; H, 3.36; N, 23.32. Found: C, 60.15; H, 3.30; N, 23.53.

EXAMPLE 17

Preparation of 4-nitro-1-(trichloromethylthio)-1H-benzotriazole

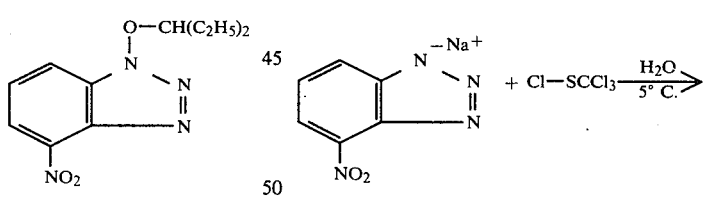

A solution of 10.2 grams of the sodium salt of 4-nitrobenzotriazole, 6 milliliters of trichloromethylsulfenyl chloride and 100 milliliters of water is stirred at 5° C. for 1 hour. The brown solid is collected by filtration and washed with ethyl ether. The crude product weighs 9.3 grams (51%) and recrystallized from carbon tetrachloride, m.p. 136.5°–137.5° C.

Analysis Calculated for $C_7H_3N_4SO_2Cl_3$: C, 26.81; H, 0.96; N, 17.81. Found: C, 27.41; H, 0.94; N, 18.10.

EXAMPLE 18

Preparation of 7-amino-1-(1-ethylpropyl)-5,6-dimethyl-1H-benzotriazole

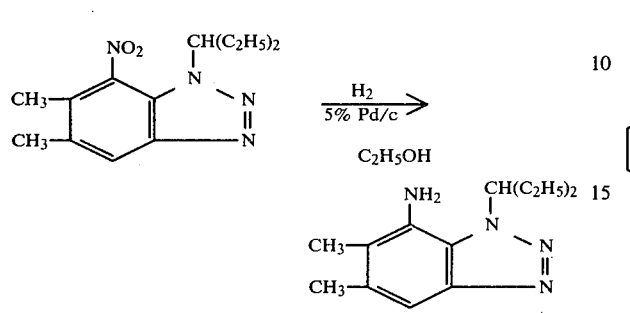

In a 1 liter Paar hydrogenator is added 3.0 grams of 5,6-dimethyl-7-nitrobenzotriazole in 250 milliliters of absolute ethanol along with 0.5 gram of 5% Pd/C. Hydrogen is introduced at about 40 psi and the reduction is accomplished without heating. The catalyst is removed by filtration and on evaporation of the solvent, 2.5 grams (94%) of the product is isolated, m.p. 114°–117° C. The analytical sample is recrystallized from n-hexane, m.p. 116°–120° C.

Analysis Calculated for $C_{13}H_{20}N_4$: C, 67.20; H, 8.68; N, 24.12. Found: C, 66.67; H, 8.70; N, 24.17.

EXAMPLE 19

Preparation of 4-Bromo-5,6-dimethyl-1H-benzotriazole

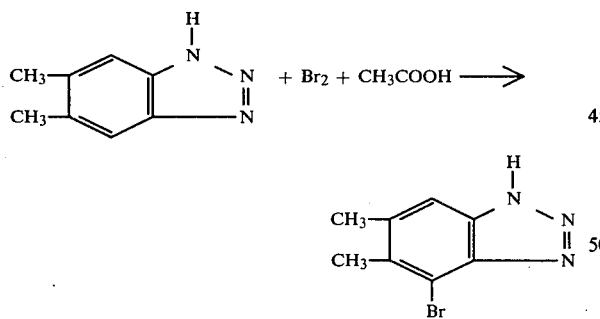

To a solution of 25.0 grams of 5,6-dimethylbenzotriazole in 250 milliliters of acetic acid at 50° C. is slowly added 30.5 grams of bromine in 75 ml. of the same solvent over a 1¼ hour period. The temperature is held at 50° C. for an additional hour and then the reaction mixture is allowed to cool to room temperature. The product is collected by filtration, 19.2 grams (56%), m.p. 255°–262° C. The analytical sample has a m.p. of 259°–261° C.

Analysis Calculated for $C_8H_8N_3Br$: C, 42.50; H, 3.57; N, 18.57. Found: C. 42.17; H, 3,47; N, 18.59.

EXAMPLE 20

Preparation of 1-(2,3-dichlorocyclohexyl)-4-nitro-1H-benzotriazole

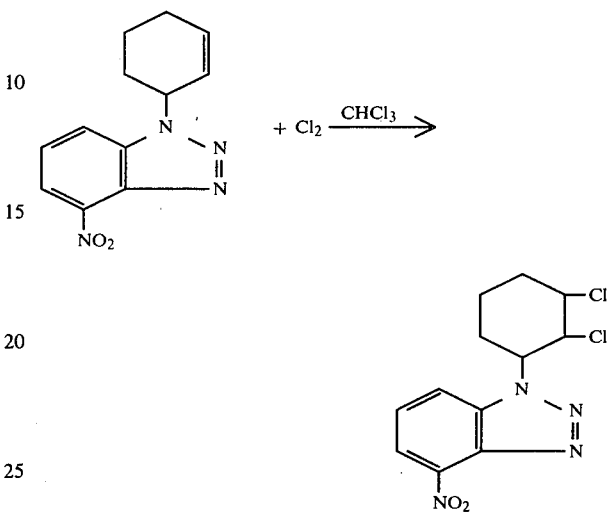

The benzotriazole is dissolved in chloroform and a 10–20% excess of chlorine gas is introduced to the stirred solution. The reaction is cooled in an ice bath as the reaction is exothermic. Then the reaction solution is filtered through Hyflo to remove any insoluble material and the chloroform evaporated to yield the crude product. The product can be recrystallized from chloroform-hexane, m.p. 145°–148° C.

Analysis Calculated for $C_{12}H_{12}N_4Cl_2O_2$: C, 45.73; H, 3.84; N, 17.78; Cl, 22.50. Found: C, 45.62; H, 3.88; N, 17.55; Cl, 22.52.

EXAMPLE 21

Preparation of 4-chloro-1-cyclohexyl-1H-benzotriazole

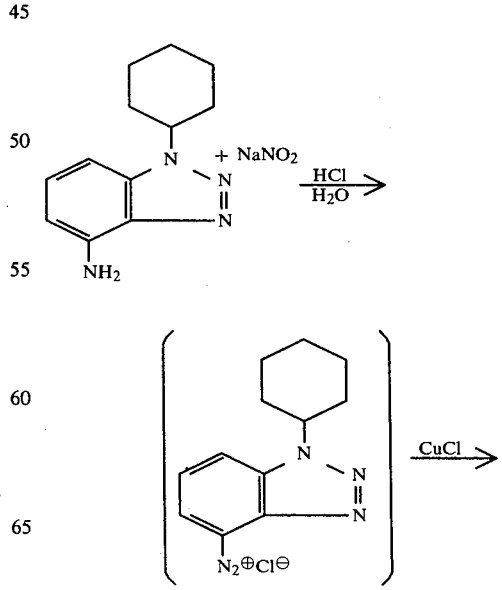

-continued

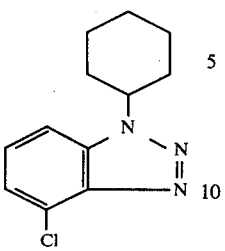

To a stirred solution of 11.4 grams of the 4-amino-1-cyclohexylbenzotriazole in 75 milliliters of concentrated hydrochloric acid and 75 milliliters of water at 5° C. is slowly added 4.1 grams of sodium nitrite in 15 milliliters of water. On completion of the addition, the reaction mixture is allowed to stir an additional ½ hour at 0°–5° C. Next the solution is added slowly to an excess of freshly prepared cuprous chloride in 120 milliliters of concentrated hydrochloric acid also at 0°–5° C. On completion of the addition, the reaction is allowed to stir and come to room temperature over a 2½ hour period. Then 1000 milliliters of water is added to the reaction mixture and the crude product is collected by filtration, washed with water and air dried. The product is purified by column chromatography, yield: 6.2 gram, m.p.=141°–144° C. The analytical sample, m.p.=146°–147° C., is recrystallized from CHCl$_3$/Et$_2$O.

Analysis Calculated for C$_{12}$H$_{14}$N$_3$Cl: C, 61.14; H, 5.99; N, 17.83; Cl, 15.04. Found: C, 60.93; H, 6.03; N, 17.83; Cl, 15.23.

EXAMPLE 22

Preparation of 4-carbonitrile-1-cyclohexyl-1H-benzotriazole

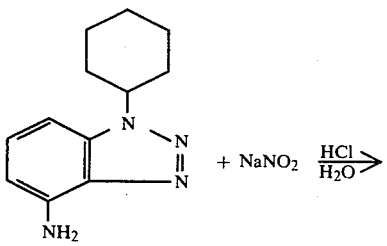

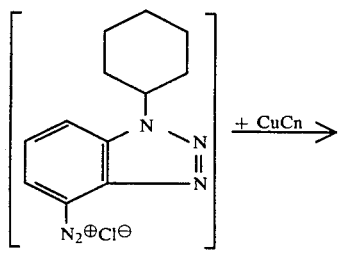

To a stirred solution of 10.2 grams of the 4-amino-1-cyclohexylbenzotriazole in 200 milliliters H$_2$O and 50 milliliters concentrated hydrochloric acid at 0°–5° C. is slowly added 3.6 grams of sodium nitrite in 20 milliliters of water. After an additional ½ hour, 20 grams of sodium carbonate is slowly added to the reaction mixture to neutralize the acid. The diazonium salt solution is then filtered cold and slowly added to an excess of freshly prepared cuprous cyanide solution in 200 milliliters water and 150 milliliters toluene at 0°–5° C. After standing at room temperature overnight, the reaction mixture is heated on the steam bath for 5–10 minutes. The toluene layer is separated, dried over magnesium sulfate and evaporated to yield 3.5 grams of a dark oily solid. The product is purified by dry column chromatography. The analytical sample is recrystallized from ethyl ether, m.p. 164°–165° C.

Analysis Calculated for C$_{13}$H$_{14}$N$_3$: C, 69.00; H, 6.24; N, 24.76. Found: C, 69.21; H, 6.32; N, 25.03.

EXAMPLE 23

Preparation of 4-methoxy-1-cyclohexyl-1H-benzotriazole

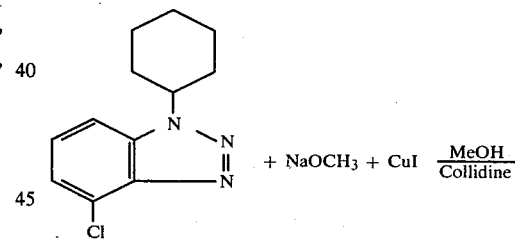

A slurry of 1.5 grams of 4-chloro-1-cyclohexylbenzotriazole, 15 grams of sodium methoxide, 10 grams of cuprous iodide in 50 milliliters of 2,4,6-trimethyl pyridine (collidine) and 10 milliliters of methanol is heated at the reflux temperature for 26 hours. The reaction is cooled and poured into 150 milliliters of 10% hydrochloric acid. The product is extracted with ethyl ether and on evaporation of the solvent, 0.5 grams of an oil is obtained which solidified on standing. The crude product is recrystallized from ethyl ether, m.p. 118°–120° C. The analytical sample has a m.p. 133°–134° C.

Analysis Calculated for $C_{13}H_{17}N_3O$: C, 67.51; H, 7.41; N, 18.17. Found: C, 67.77; H, 7.54; N, 18.37.

EXAMPLE 24

Preparation of 4-Acetamido-1-sec-butyl-1H-benzotriazole, hydrochloride

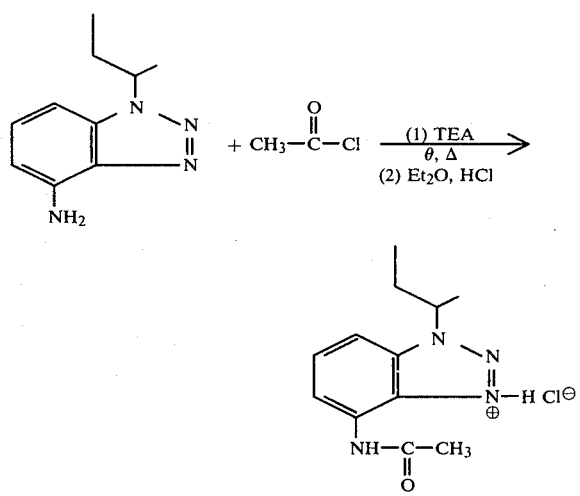

To a stirred solution of 3.8 grams of the 4-aminobenzotriazole and 3.0 grams of triethylamine in 50 milliliters of benzene is slowly added 1.6 grams of acetyl chloride in 10 milliliters of the same solvent. After the exotherm subsides, the reaction is heated to the reflux temperature for two hours. The reaction is cooled, the triethylamine hydrochloride is removed by filtration and the filtrate evaporated to yield 5.2 grams of an oil. The oil is dissolved in ethyl ether and treated with a saturated HCl . methanolic solution. The product precipitates from the solution on cooling, and can be recrystallized from acetonitrile, m.p.=170°–184° C.

Analysis Calculated for $C_{12}H_{16}N_4O \cdot HCl$: C, 53.63; H, 6.38; N, 20.85. Found: C, 53.37; H, 6.27; N, 21.05.

EXAMPLE 25

Preparation of 4-isothiocyano- 1 sec-butyl-1H-benzotriazole

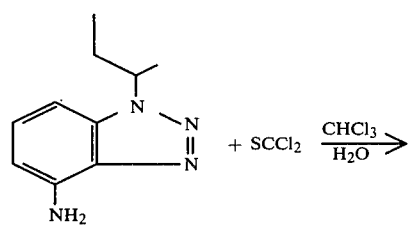

To a stirred solution of 3.5 grams thiophosgene in 50 milliliters chloroform and 100 milliliters water is slowly added 4.8 grams of the benzotriazole in 75 milliliters of chloroform. Neutrality is maintained by the addition of calcium carbonate. After one hour the chloroform layer is dried over calcium chloride and evaporated to yield 6.3 grams of oil which solidifies on cooling. The product is recrystallized from n-hexane, m.p.=77°–78° C.

Analysis Calculated for $C_{11}H_{12}N_4S$: C, 56.87; H, 5.21; N, 24.12; S, 13.80. Found: C, 56.88; H, 5.24; N, 24.22; S, 13.60.

EXAMPLES 26 & 27

Preparation of Cyclohexanol, 2-(4-nitro-1H-benzotriazol-1-yl) and Cyclohexanol, 2-(4-nitro-2H-benzotriazol-2-yl)-

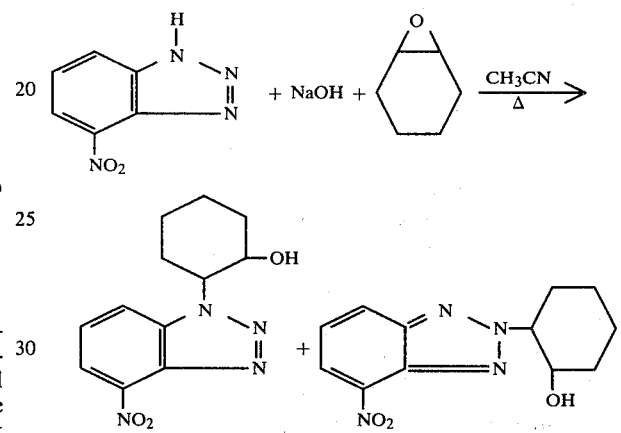

A mixture of 60 grams of 4-nitrobenzotriazole, 16 grams sodium hydroxide "Pels" and 1500 milliliters of acetonitrile is heated to 60° C. The cyclohexene oxide is then slowly added and the solution is heated at the reflux temperature for 48 hours. After cooling, the reaction is filtered and the acetonitrile evaporated to yield an oily residue. The 2-alkyl isomer is extracted with ethyl ether leaving behind the 1-alkyl isomer as a crude solid.

The 1-alkyl isomer is recrystallized from methanol, m.p. 205°–206° C. Analysis Calculated for $C_{12}H_{14}N_4O_3$: C, 54.96; H, 5.40; N, 21.26. Found: C, 54.95; H, 5.13; N, 21.54.

The 2-alkyl isomer is recrystallized from carbon tetrachloride, m.p. 139°–141° C. Analysis Calculated for $C_{12}H_{14}N_4O_3$: C, 54.95; H, 5.40; N, 21.36. Found: C, 54.56; H, 5.19; N, 21.56.

EXAMPLE 28

Preparation of Cyclohexanol, 2-(4-nitro-1H-benzotriazol-1-yl)-, formate ester

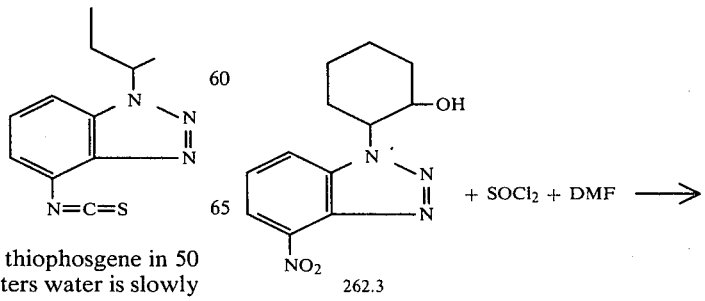

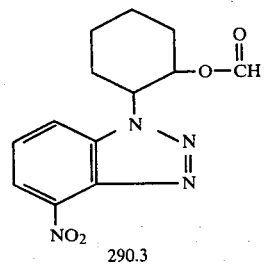

290.3

To a solution of one gram of the benzotriazole in 10 milliliters of dimethylformamide is slowly added a mixture of 0.6 grams thionyl chloride and 3 milliliters of dimethylformamide. The reaction is cooled in an ice bath. The reaction is allowed to stand at room temperature for overnight. Then the reaction mixture is poured into 140 milliliters of cold water and the product crystallized from solution. The product is collected by filtration and air dried, m.p. 136°–137° C.

Analysis Calculated for $C_{13}H_{14}N_4O_4$: C, 53.79; H, 4.86; N, 19.30. Found: C, 53.43; H, 4.92; N, 19.36.

EXAMPLES 29–49

Preparation of 1H-benzotriazoles

Other 1H-benzotriazoles of the present invention can be prepared by the procedures heretofore described. These benzotriazoles are listed on Table I below, where they are characterized by melting points. The procedure used for synthesis of each compound is identified by example number and each compound is prepared by substituting the appropriate intermediates into the procedure of the example identified.

TABLE I

1H-Benzotriazoles

| EXAMPLE NO. | $R_1$ | $R_4$ | $R_5$ | $R_6$ | $R_7$ | °C. m.p. | EXAMPLE PROCEDURE |
|---|---|---|---|---|---|---|---|
| 29 | $CH(CH_3)_2$ | $NO_2$ | H | H | H | 99–100 | 9 |
| 30 | $CH_2$ | $NO_2$ | H | H | H | 99–100 | 9 |
| 31 | $CH(CH_3)C_2H_5$ | $NO_2$ | H | H | H | 78–79 | 5 |
| 32 | $CH(C_2H_5)_2$ | $NO_2$ | H | H | H | 132–134 | 5 |
| 33 | $CH(CH_3)C_3H_7$ | $NO_2$ | H | H | H | 60–70 | 5 |
| 34 | cyclohexenyl | $NO_2$ | H | H | H | 130–132 | 9 |
| 35 | cyclopropyl | $NO_2$ | H | H | H | 160–163 | 5 |
| 36 | cycloheptyl | $NO_2$ | H | H | H | 82–84 | 9 |
| 37 | $CH(CH_3)_2$ | H | H | H | H | 106–107 at 1.0 mm Hg | 1 |
| 38 | $CH_2\phi$ | H | H | H | H | 113–114 | 1 |
| 39 | 2-methylcyclohexyl | $NO_2$ | H | H | H | 105–107 | 5 |
| 40 | 4-methylcyclohexyl | $NO_2$ | H | H | H | 152–154 | 5 |
| 41 | $CH(C_3H_7)_2$ | $NO_2$ | H | H | H | 49.5–50.5 | 5 |
| 42 | cyclohexyl | $NO_2$ | H | H | H | 163–165 | 5 |
| 43 | cyclopentyl | $NO_2$ | H | H | H | 80–81 | 9 |
| 44 | $-(CH_2)_5CH_3$ | $NO_2$ | H | H | H | 72–73 | 9 |
| 45 | $-CH(C_2H_5)CH_2OCH_3$ | $NO_2$ | H | H | H | 87–89 | 5 |

TABLE I-continued

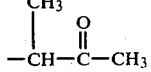

1H-Benzotriazoles

| EXAMPLE NO. | R₁ | R₄ | R₅ | R₆ | R₇ | °C. m.p. | EXAMPLE PROCEDURE |
|---|---|---|---|---|---|---|---|
| 46 | —CH(CH₃)—C(O)—CH₃ | NO₂ | H | H | H | 110–112 | 9 |
| 47 | cycloheptyl | NO₂ | H | H | H | 109–111 | 5 |
| 48 | CH₂-cyclohexyl | NO₂ | H | H | H | 101–102 | 9 |
| 49 | C(CH₃)₃ | NO₂ | H | H | H | 179–180 | 5 |

EXAMPLE 56

Preparation of 2H-Benzotriazoles

Other 2H-benzotriazoles that can be prepared in accordance with process of the present invention are listed in Table II below. Melting points for compounds prepared are listed in said table along with the example number of the procedure used to prepare said compound.

TABLE II

2H-Benzotriazoles

| EXAMPLE NO. | R₂ | R₄ | R₅ | R₆ | R₇ | °C. m.p. or b.p. | EXAMPLE PROCEDURE |
|---|---|---|---|---|---|---|---|
| 50 | CH(CH₃)C₂H₅ | NO₂ | H | H | H | oil | 6 |
| 51 | CH₂φ | NO₂ | H | H | H | 91–93 | 9 |
| 52 | CH(C₂H₅)₂ | NO₂ | H | H | H | 90–92 | 9 |
| 53 | cyclohexyl | NO₂ | H | H | H | 78–81 | 6 |
| 54 | cycloheptyl | NO₂ | H | H | H | 90–91 | 9 |
| 55 | cyclopentyl | NO₂ | H | H | H | 60–62 | 9 |
| 56 | CH₂-cyclohexyl | NO₂ | H | H | H | 131–133 | 9 |
| 57 | CH(CH₃)₂ | NO₂ | H | H | H | 65–67 | 6 |

EXAMPLE 57

Preparation of
2-(4-Nitro-1H-benzotriazol-1-yl)-cyclohexanol and
2-(4-Nitro-2H-benzotriazol-2-yl)-cyclohexanol.

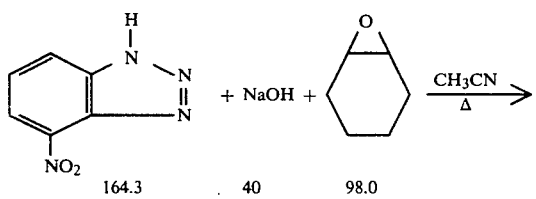

A mixture of 4-nitrobenzotriazole (60.0 g, 0.37 mol), sodium hydroxide "Pels" (16.0 g, 0.40 mol) and 1500 ml of acetonitrile was heated to 60°. The cyclohexene oxide (80.0 g, 0.81 mol) was then slowly added and the solution heated at the reflux temperature for 48 hours. After cooling, the reaction was filtered and the acetonitrile evaporated to yield an oily residue. The 2-alkyl isomer was extracted with ethyl ether leaving behind the 1-alkyl isomer as a solid.

EXAMPLE 58

Preparation of
1-(2-Methoxycyclohexyl)-4-nitro-1H-benzotriazole.

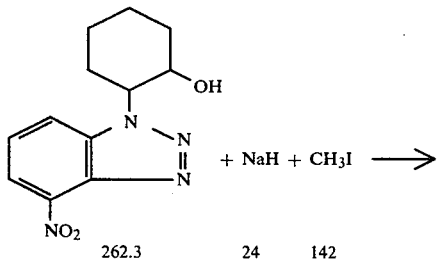

To a slurry of the hydroxy compound (3.5 g, 0.014 mol) in 100 ml of dry dimethoxyethane was added a mineral oil dispersion of 57% sodium hydride (0.85 g) at 40°. After the evolution of hydrogen had subsided, methyl iodide (6.0 g, 0.040 mol) was added over a 15-minute period. After 1½ hours, tlc indicated starting material still present and therefore additional sodium hydride (0.49 g) and methyl iodide (3.0 g, 0.20 mol) was added. After an additional 2 hours, tlc showed no starting material. The reaction mixture was filtered and the solvent evaporated to yield a dark oil.

The crude product was purified by dry column chromatography using chloroform as the developing solvent. The analytical sample, m.p. 134°-136°, was recrystallized from ethanol.

EXAMPLE 59

Preparation of
4-Chloro-1-cyclohexyl-1H-benzotriazole.

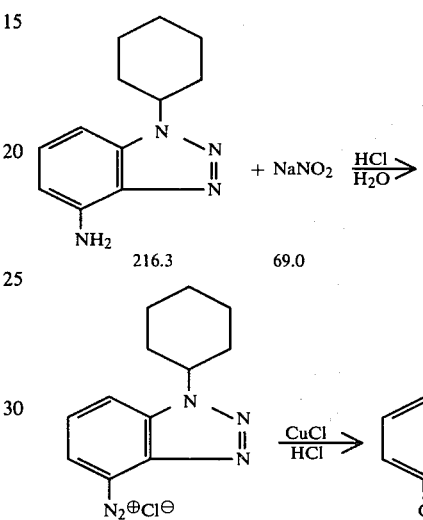

To a stirred solution of the 4-amino-1-cyclohexylbenzotriazole (11.4 g, 0.054 mol) in 75 ml of concentrated hydrochloric acid and 75 ml of water at 5°, was slowly added 4.1 g of sodium nitrite (0.059 mol) in 15 ml of water. On completion of the addition, the reaction mixture was allowed to stir an additional ½ hour at 0°-5°. Next the solution was added slowly to an excess of freshly prepared cuprous chloride in 120 ml of concentrated hydrochloric acid also at 0°-5°. On completion of the addition, the reaction came to room temperature over a 2½ hour period. Then one liter of water was added to the reaction mixture and the crude product which precipitated was collected by filtration, washed with water and air-dried. This material was purified by column chromatography to yield 6.2 g of product, m.p. 141°-144°.

EXAMPLE 60

Preparation of
4-Methoxy-1-cyclohexyl-1H-benzotriazole.

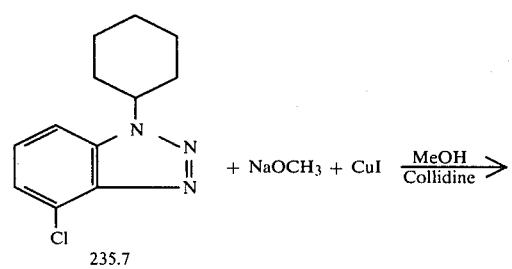

-continued

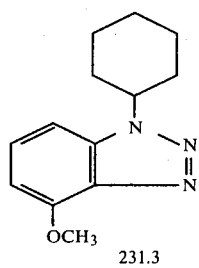

231.3

A slurry of 1.5 g of 4-chloro-1-cyclohexylbenzotriazole, 15 g of sodium methoxide, 10 g of cuprous iodide in 50 ml of 2,4,6-trimethyl pyridine (collidine) and 10 ml of methanol was heated at the reflux temperature for 26 hours. The reaction was cooled and poured into 150 ml of 10% hydrochloric acid. The product was extracted with ethyl ether and on evaporation of the solvent, 0.5 g of a oil was obtained which solidified on standing. The product has a melting point of 133°–134°.

EXAMPLE 61

The postemergence herbicidal activity of the compounds of the present invention is demonstrated by the following tests, wherein a variety of monocotyledonous and dicotyledonous plants are treated with test compounds dispersed in aqueous acetone mixtures In the tests, seedling plants are grown in plastic pots arranged in Jiffy ® flats for about two weeks. The test compounds are dispersed in 50/50 acetone/water mixtures in sufficient quantity to provide the equivalent of about 0.25 lb. to 4 lbs. per acre of active compound when applied to the plants through a spray nozzle operating at 40 psi for a predetermined time. After spraying, the plants are placed on greenhouse benches and are cared for in the usual manner, commensurate with conventional greenhouse practices. Three to five weeks after treatment, the seedling plants are examined and rated according to the rating system provided below. The data obtained are reported in Tables III, IV, where it can be seen that the compounds are effective for the postemergence control of a variety of broadleaf weeds and grass weeds.

| Rating System: | % Difference in Growth from the Check* |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |

4 = abnormal growth, that is, a definite physiological malformation but with an over-all effect less than a 5 on the rating scale.
*Based on visual determination of stand, size, vigor, chlorosis, growth malformation and over-all plant appearance.

| Plant Species Employed in Evaluations | | |
|---|---|---|
| Common Name | Abbreviation | Scientific Name |
| Lambsquarters | LA | Chenopodium album |
| Wild Mustard | MU | Brassica Kaber |
| Pigweed | PI | Amaranthus retroflexus |
| Ragweed | RW | Ambrosia artemisiifolia |
| Morning glory | MG | Ipomoaea purpurea |
| Barnyardgrass | BA | Echinochloa crusgalli |
| Crabgrass | CR | Digitaria sanguinalis |
| Green Foxtail | FO | Setaria viridis |
| Wild Oats | WO | Avena fatua |
| Corn | CN | Zea mays |
| Cotton | CO | Gossypium hirsutum |
| Soybean | SY | Glycine max |
| Rice | RI | Oryza sativa |

TABLE III

POSTEMERGENCE HERBICIDAL ACTIVITY OF 1H-BENZOTRIAZOLES HAVING THE STRUCTURE

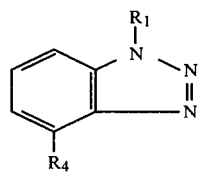

| STRUCTURE | | RATE LBS./ | PLANT SPECIES | | | | | | | | | | | | |
|---|---|---|---|---|---|---|---|---|---|---|---|---|---|---|---|
| $R_1$ | $R_4$ | ACRE | LA | MU | PI | RW | MG | BA | CR | FO | WO | CN | CU | SY | RI |
| —CH₂—⟨phenyl⟩ | NO₂ | 4 | 9 | 9 | 9 | 8 | 9 | 9 | 9 | 9 | 1 | 1 | 9 | 1 | 2 |
| | | 1 | 9 | 9 | 9 | 3 | 9 | 6 | 9 | 7 | 1 | 0 | 9 | 0 | 1 |
| | | 0.5 | 9 | 9 | 9 | 0 | 2 | 2 | 9 | 3 | 0 | 0 | 1 | 0 | 1 |
| —CH(CH₃)₂ | NO₂ | 4 | 9 | 9 | 9 | 5 | 9 | 9 | 9 | 9 | 2 | 1 | 9 | 3 | 2 |
| | | 1 | 9 | 9 | 9 | 0 | 2 | 8 | 9 | 9 | 1 | 0 | 8 | 1 | 1 |
| | | 0.5 | 9 | 9 | 9 | 0 | 3 | 1 | 9 | 7 | 1 | 0 | 7 | 0 | 1 |
| —CH(C₂H₅)₂ | NO₂ | 1 | 9 | 9 | 9 | 9 | 9 | 9 | 9 | 9 | 1 | 0 | 9 | 5 | 2 |
| | | 0.5 | 9 | 9 | 9 | 0 | 9 | 2 | 9 | 8 | 1 | 0 | 9 | 1 | 2 |
| | | 0.25 | 9 | 9 | 9 | 0 | 9 | 5 | 9 | 3 | 1 | 1 | 0 | 1 | 1 |
| —CH(CH₃)C₂H₅ | NO₂ | 1 | 9 | 9 | 9 | 8 | 9 | 9 | 9 | 9 | 6 | 7 | 9 | 7 | 2 |
| | | 0.5 | 9 | 9 | 9 | 2 | 9 | 9 | 9 | 8 | 3 | 7 | 9 | 3 | 2 |
| | | 0.25 | 6 | 9 | 9 | 0 | 9 | 7 | 9 | 6 | 2 | 2 | 5 | 0 | 1 |
| —⟨cyclopentyl⟩ | NO₂ | 4 | 9 | 9 | 9 | 9 | 9 | 9 | 9 | 8 | 8 | 2 | 9 | 7 | 9 |
| | | 1 | 3 | 9 | 3 | 9 | 2 | 7 | 9 | 2 | 2 | 1 | 3 | 2 | 2 |

TABLE III-continued

POSTEMERGENCE HERBICIDAL ACTIVITY OF 1H-BENZOTRIAZOLES HAVING THE STRUCTURE

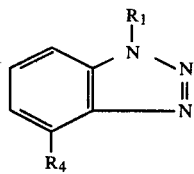

| STRUCTURE $R_1$ | $R_4$ | RATE LBS./ACRE | PLANT SPECIES ||||||||||||
|---|---|---|---|---|---|---|---|---|---|---|---|---|---|---|
| | | | LA | MU | PI | RW | MG | BA | CR | FO | WO | CN | CU | SY | RI |
| cyclohexyl-CH₃ (4-methyl) | NO₂ | 2 | 7 | 9 | 9 | 8 | 9 | 6 | 6 | 3 | 1 | — | — | — | — |
| | | 1 | 5 | 8 | 9 | 0 | 2 | 3 | 6 | 1 | 0 | — | — | — | — |
| cyclohexyl-CH₃ (3-methyl) | NO₂ | 1 | 9 | 9 | 9 | 9 | 9 | 9 | 7 | 7 | 6 | — | — | — | — |
| | | 0.25 | 9 | 8 | 9 | 0 | 9 | 7 | 7 | 1 | 1 | — | — | — | — |
| cyclohexyl-Cl,Cl | NO₂ | 1 | 9 | 9 | 9 | 9 | 9 | 9 | 9 | 9 | 5 | — | — | — | — |
| | | 0.25 | 5 | 9 | 9 | 8 | 9 | 9 | 9 | 8 | 3 | — | — | — | — |
| cyclohexyl | NO₂ | 1 | 9 | 9 | 9 | 9 | 9 | 9 | 9 | 9 | 2 | 3 | 9 | 5 | 3 |
| | | 0.5 | 9 | 9 | 9 | 9 | 9 | 8 | 7 | 8 | 1 | 2 | 9 | 5 | 3 |
| | | 0.25 | 9 | 9 | 9 | 0 | 9 | 7 | 7 | 7 | 1 | 1 | 9 | 5 | 2 |
| —CH(C₃H₇-n)₂ | NO₂ | 4 | 9 | 9 | 9 | 0 | 2 | 3 | 7 | 2 | 1 | 0 | 1 | 2 | 1 |
| | | 1 | 0 | 5 | 5 | 0 | 2 | 1 | 3 | 1 | 0 | 0 | 0 | 1 | 0 |
| —CH₂-cyclohexyl | NO₂ | 1 | 9 | 9 | 9 | 0 | 9 | 9 | 9 | 9 | 1 | 2 | 9 | 2 | 3 |
| | | 0.5 | 9 | 8 | 9 | 0 | 9 | 7 | 7 | 7 | 1 | 1 | 7 | 1 | 3 |
| | | 0.25 | 8 | 8 | 9 | 0 | 9 | 6 | 3 | 5 | 0 | 0 | 3 | 0 | 3 |
| cyclohexenyl | NO₂ | 1 | 9 | 9 | 9 | 9 | 9 | 7 | 9 | 9 | 2 | 1 | 9 | 2 | 5 |
| | | 0.5 | 9 | 9 | 9 | 9 | 9 | 7 | 7 | 8 | 1 | 1 | 7 | 1 | 3 |
| | | 0.25 | 8 | 7 | 9 | 2 | 3 | 5 | 3 | 3 | 0 | 1 | 7 | 1 | 3 |
| cycloheptyl | NO₂ | 1 | 9 | 9 | 9 | 9 | 9 | 9 | 9 | 9 | 2 | 2 | 9 | 9 | 2 |
| | | 0.5 | 8 | 9 | 9 | 7 | 9 | 9 | 7 | 3 | 1 | 2 | 9 | 6 | 5 |
| | | 0.25 | 7 | 7 | 9 | 2 | 9 | 3 | 7 | 1 | 1 | 1 | 9 | 2 | 3 |
| cycloheptyl | NO₂ | 1 | 9 | 9 | 9 | 9 | 9 | 9 | 9 | 8 | 6 | 3 | 9 | 3 | 5 |
| | | 0.25 | 7 | 9 | 9 | 0 | 9 | 7 | 7 | 7 | 2 | 3 | 3 | 3 | 5 |
| cyclohexyl-OH | NO₂ | 1 | 8 | 9 | 9 | 3 | 9 | 5 | 3 | 3 | 2 | 3 | 9 | 7 | 5 |
| | | 0.25 | 3 | 9 | 9 | 0 | 2 | 2 | 2 | 1 | 1 | 3 | 7 | 3 | 3 |
| cyclohexyl-OCHO | NO₂ | 4 | 9 | 9 | 9 | 9 | 9 | 9 | 3 | 5 | 2 | 3 | 6 | 9 | 7 |
| | | 1 | 5 | 9 | 9 | 9 | 9 | 2 | 7 | 9 | 1 | 2 | 5 | 5 | 7 |
| —CH(CH₃)C₂H₅ | SCN | 3 | 9 | 9 | 9 | 7 | 9 | 3 | 6 | 5 | 3 | 9 | 5 | 7 | 2 |
| | | 1 | 9 | 8 | 9 | 7 | 3 | 1 | 3 | 2 | 1 | 7 | 0 | 5 | 2 |
| cyclohexyl | CN | 4 | 9 | 9 | 9 | 3 | 7 | 7 | 6 | 3 | 3 | 3 | 3 | 8 | 5 |
| | | 1 | 9 | 9 | 9 | 0 | 8 | 3 | 3 | 2 | 2 | 3 | 7 | 7 | 5 |
| | | 0.5 | 9 | 9 | 9 | 8 | 8 | 2 | 2 | 2 | 3 | 3 | 3 | 5 | 5 |

TABLE III-continued
POSTEMERGENCE HERBICIDAL ACTIVITY OF 1H-BENZOTRIAZOLES HAVING THE STRUCTURE

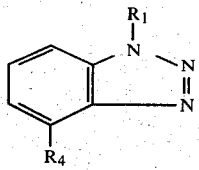

| STRUCTURE R₁ | R₄ | RATE LBS./ACRE | LA | MU | PI | RW | MG | BA | CR | FO | WO | CN | CU | SY | RI |
|---|---|---|---|---|---|---|---|---|---|---|---|---|---|---|---|
| cyclohexyl | Cl | 4 | 9 | 9 | 9 | 9 | 8 | 9 | 9 | 9 | 9 | 5 | 7 | 9 | 7 |
| | | 1 | 9 | 9 | 9 | 9 | 8 | 9 | 9 | 9 | 9 | 6 | 7 | 7 | 7 |
| | | 0.5 | 9 | 9 | 9 | 3 | 9 | 9 | 9 | 9 | 9 | 9 | 6 | 6 | 3 |
| cyclohexyl | OCH₃ | 4 | 9 | 9 | 9 | 9 | 8 | 9 | 9 | 9 | 8 | — | — | — | — |
| cyclohexyl-OCH₃ | NO₂ | 4 | — | 7 | 7 | 9 | 1 | 3 | 1 | 1 | — | 2 | 5 | 3 | 5 |
| —CO—CH₂Cl | NO₂ | 4 | 8 | 9 | 7 | 0 | 2 | 6 | 8 | 7 | 9 | 8 | 5 | 5 | 6 |
| —CH(CH₃)—COCH₃ | NO₂ | 4 | 9 | 7 | 9 | 3 | 9 | 2 | 7 | 2 | 0 | 0 | 1 | 2 | 2 |
| —CH(CH₃)—C₃H₇-n | NO₂ | 4 | 9 | 9 | 9 | 9 | 9 | 9 | 6 | 7 | 7 | 7 | 9 | 9 | 5 |
| | | 1 | 8 | 9 | 9 | 7 | 8 | 5 | 3 | 2 | 2 | 2 | 7 | 8 | 6 |
| —O—CH(CH₃)C₂H₅ | NO₂ | 9* | 9 | 9 | 9 | 5 | 3 | 8 | 3 | 1 | 1 | 2 | 9 | 2 | 1 |
| | | 3 | 0 | 9 | 9 | 0 | 1 | 1 | 2 | 1 | 0 | 0 | 3 | 2 | 0 |
| —CO—CH(CH₃)₂ | NO₂ | 4 | 9 | 9 | 9 | 1 | 0 | 7 | 6 | 2 | 1 | — | — | — | — |
| —CH(C₂H₅)CH₂—O—CH₃ | NO₂ | 4 | 9 | 9 | 9 | 2 | 9 | 7 | 7 | 6 | 1 | 2 | 7 | 6 | 2 |
| | | 1 | 5 | 8 | 9 | 0 | 8 | 6 | 6 | 2 | 0 | 1 | 5 | 5 | 2 |
| —OCH(CH₃)₂ | NO₂ | 4 | 1 | 7 | 9 | 1 | 1 | 7 | 7 | 7 | 0 | 0 | 1 | 1 | 0 |
| —C(CH₃)₃ | NO₂ | 4 | 9 | 2 | 9 | 9 | 3 | 7 | 7 | 7 | 1 | 1 | 1 | 1 | 1 |
| | | 1 | 7 | 3 | 8 | 0 | 3 | 3 | 5 | 2 | 1 | 1 | 0 | 0 | 0 |

*RUN BY SAME PROCEDURE BUT AT 9 lb/A

TABLE IV

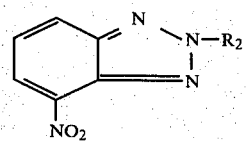

POSTEMERGENCE HERBICIDAL ACTIVITY OF 2H-BENZOTRIAZOLES HAVING THE ABOVE STRUCTURE

| STRUCTURE R₂ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH(CH₃)₂ | 4 | 9 | 9 | 9 | 9 | 9 | 9 | 9 | 9 | 2 | 3 | 9 | 9 | 5 |
| | 1 | 9 | 9 | 9 | 0 | 9 | 8 | 9 | 9 | 1 | 1 | 9 | 1 | 1 |
| | 0.5 | 1 | 8 | 9 | 0 | 5 | 6 | 7 | 7 | 0 | 1 | 3 | 1 | 0 |
| —CH(CH₃)C₂H₅ | 1 | 9 | 9 | 9 | 0 | 1 | 9 | 9 | 9 | 2 | 1 | 3 | 1 | 1 |
| | 0.5 | 9 | 9 | 9 | 0 | 3 | 8 | 9 | 9 | 0 | 1 | 2 | 1 | 1 |
| | 0.25 | 0 | 9 | 9 | 0 | 0 | 3 | 9 | 9 | 0 | 0 | 1 | 0 | 0 |
| —CH₂—phenyl | 4 | 9 | 9 | 9 | 0 | 9 | 5 | 9 | 3 | 1 | 1 | 3 | 0 | 1 |
| | 1 | 7 | 9 | 9 | 0 | 7 | 2 | 9 | 2 | 0 | 1 | 1 | 0 | 1 |
| —CH(C₂H₅)₂ | 4 | 9 | 9 | 9 | 5 | 9 | 9 | 9 | 9 | 1 | 2 | 9 | 3 | 1 |
| | 1 | 9 | 3 | 9 | 0 | 9 | 8 | 9 | 9 | 1 | 5 | 9 | 3 | 1 |
| | 0.5 | 7 | 3 | 9 | 0 | 2 | 7 | 9 | 9 | 0 | 2 | 3 | 3 | 0 |
| cyclopentyl | 4 | 9 | 9 | 9 | 9 | 5 | 9 | 9 | 7 | 3 | 2 | 2 | 2 | 5 |
| cyclohexenyl | 4 | 9 | 9 | 9 | 0 | 1 | 6 | 9 | 7 | 1 | 3 | 7 | 2 | 1 |

TABLE IV-continued

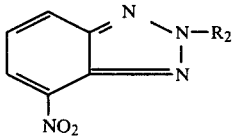

POSTEMERGENCE HERBICIDAL ACTIVITY OF
2H-BENZOTRIAZOLES HAVING THE ABOVE STRUCTURE

| STRUCTURE R₂ | RATE LBS./ACRE | LA | MU | PI | RW | MG | BA | CR | FO | WO | CN | CO | SY | RI |
|---|---|---|---|---|---|---|---|---|---|---|---|---|---|---|
| cyclohexyl | 4 | 7 | 9 | 9 | 1 | 3 | 3 | 8 | 3 | 2 | 2 | 5 | 6 | 2 |
| cyclohexyl | 4 | 7 | 7 | 9 | 0 | 6 | 6 | 6 | 2 | 3 | 2 | 3 | 3 | 3 |
| cyclohexyl-OH | 4 | 8 | 8 | 9 | 3 | 3 | 6 | 3 | 6 | 0 | 1 | 2 | 3 | 1 |
| | 1 | 3 | 7 | 9 | 0 | 2 | 2 | 2 | 2 | 0 | 2 | 2 | 3 | 1 |
| —CH₂CH₂CH₂CN | 4 | 9 | 9 | 7 | 0 | 1 | 2 | 7 | 3 | 0 | 1 | 1 | 2 | 0 |
| cyclopentyl | 4 | 9 | 9 | 9 | 9 | 5 | 9 | 9 | 7 | 3 | 2 | 2 | 2 | 5 |
| CH₂-cyclohexyl | 4 | 9 | 7 | 9 | 2 | 8 | 7 | 7 | 7 | 1 | 1 | 8 | 2 | 3 |

EXAMPLE 62

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.25 to .4 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the Tables V, VI and VII below.

TABLE V

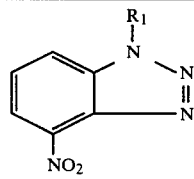

PREEMERGENCE HERBICIDAL ACTIVITY OF 1H-BENZOTRIAZOLES
HAVING THE ABOVE STRUCTURE

| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH₂—phenyl | 4 | 5 | 7 | 9 | 7 | 0 | 9 | 9 | 9 | 0 | 0 | 0 | 0 | 0 |
| | 1 | 0 | 0 | 7 | 0 | 0 | 7 | 8 | 0 | 0 | 0 | 0 | 0 | 0 |
| —CH(CH₃)₂ | 4 | 7 | 7 | 3 | 7 | 0 | 9 | 9 | 7 | 0 | 0 | 0 | 0 | 7 |
| | 1 | 0 | 0 | 3 | 0 | 0 | 6 | 5 | 0 | 0 | 0 | 0 | 0 | 1 |
| —CH(C₂H₅)₂ | 4 | 9 | 9 | 9 | 9 | 2 | 9 | 9 | 9 | 0 | 0 | 2 | 0 | 8 |
| | 1 | 9 | 9 | 9 | 9 | 0 | 9 | 9 | 8 | 0 | 0 | 0 | 0 | 8 |
| | 0.5 | 9 | 0 | 9 | 7 | 1 | 9 | 9 | 6 | 0 | 0 | 0 | 0 | 4 |
| —CH(CH₃)C₂H₅ | 1 | 8 | 0 | 8 | 8 | 5 | 9 | 9 | 8 | 0 | 0 | 0 | 0 | 9 |
| | 0.5 | 4 | 0 | 7 | 5 | 0 | 8 | 8 | 5 | 0 | 0 | 0 | 0 | 5 |

TABLE V-continued
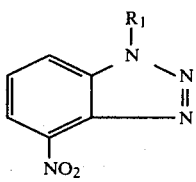
PREEMERGENCE HERBICIDAL ACTIVITY OF 1H-BENZOTRIAZOLES
HAVING THE ABOVE STRUCTURE
| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| cyclopentyl | 4 | 9 | 9 | 9 | 9 | 5 | 9 | 9 | 9 | 8 | 0 | 0 | 0 | 9 |
|  | 1 | 9 | 9 | 9 | 9 | 0 | 9 | 9 | 9 | 1 | 0 | 0 | 0 | 2 |
|  | 0.5 | 9 | 9 | 9 | 9 | 0 | 9 | 9 | 9 | 0 | 0 | 0 | 0 | 0 |
| 2-methylcyclohexyl | 1 | 9 | 9 | 9 | 9 | 2 | 9 | 9 | 9 | 7 | 2 | 6 | 0 | 7 |
|  | 0.25 | 9 | 3 | 8 | 5 | 0 | 6 | 9 | 5 | 2 | 0 | 0 | 0 | 1 |
| 2,3-dichlorocyclohexyl | 1 | 9 | 9 | 9 | 9 | 9 | 9 | 9 | 9 | 7 | 6 | 7 | 3 | 8 |
|  | 0.25 | 9 | 8 | 9 | 8 | 0 | 8 | 9 | 9 | 3 | 0 | 0 | 0 | 2 |
| cyclohexyl | 1 | 9 | 9 | 9 | 9 | 9 | 9 | 9 | 9 | 2 | 3 | 9 | 5 | 3 |
|  | 0.5 | 9 | 9 | 9 | 9 | 9 | 9 | 9 | 9 | 1 | 2 | 9 | 5 | 3 |
|  | 0.25 | 9 | 9 | 9 | 0 | 9 | 9 | 9 | 9 | 1 | 1 | 9 | 5 | 2 |
| cycloheptyl | 1 | 9 | 9 | 9 | 9 | 9 | 9 | 9 | 9 | 7 | 1 | 2 | 1 | 3 |
|  | 0.5 | 9 | 6 | 8 | 9 | 0 | 9 | 9 | 9 | 4 | 0 | 0 | 0 | 3 |
|  | 0.25 | 9 | 6 | 9 | 9 | 0 | 8 | 9 | 6 | 4 | 0 | 0 | 0 | 3 |
| CH₂-cyclopentyl | 1 | 9 | 7 | 9 | 9 | 0 | 9 | 9 | 9 | 1 | 1 | 5 | 0 | 2 |
|  | 0.5 | 9 | 0 | 9 | 0 | 0 | 9 | 9 | 7 | 0 | 0 | 0 | 0 | 0 |
|  | 0.25 | 9 | 0 | 8 | 0 | 0 | 7 | 5 | 2 | 0 | 0 | 2 | 0 | 0 |
| cyclohexenyl | 1 | 9 | 9 | 9 | 9 | 5 | 9 | 9 | 9 | 8 | 0 | 0 | 0 | 9 |
|  | 0.5 | 9 | 9 | 9 | 9 | 0 | 9 | 9 | 9 | 1 | 0 | 0 | 0 | 2 |
|  | 0.25 | 9 | 9 | 9 | 9 | 0 | 9 | 9 | 9 | 0 | 0 | 0 | 0 | 0 |
| cyclooctyl | 1 | 9 | 9 | 9 | 9 | 2 | 9 | 9 | 9 | 7 | 3 | 0 | 0 | 6 |
|  | 0.25 | 9 | 0 | 9 | 8 | 0 | 9 | 9 | 8 | 2 | 0 | 0 | 0 | 2 |
| 2-hydroxycyclohexyl | 1 | 9 | 9 | 9 | 9 | 5 | 8 | 9 | 8 | 1 | 2 | 5 | 0 | 8 |
|  | 0.25 | 5 | 7 | 9 | 2 | 0 | 6 | 6 | 3 | 0 | 0 | 0 | 0 | 6 |
| 2-formyloxycyclohexyl | 1 | 9 | 9 | 9 | 9 | 2 | 8 | 8 | 9 | 2 | 3 | 3 | 5 | 9 |
|  | 0.25 | 7 | 8 | 9 | 6 | 0 | 7 | 6 | 6 | 0 | 0 | 2 | 0 | 3 |

TABLE VI

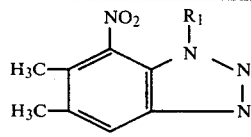

PREEMERGENCE HERBICIDAL ACTIVITY OF 1H-BENZOTRIAZOLES HAVING THE ABOVE STRUCTURE

| STRUCTURE R₁ | RATE LBS./ACRE | LA | MU | PI | RW | MG | BA | CR | FO | WO | CN | CO | SY | RI |
|---|---|---|---|---|---|---|---|---|---|---|---|---|---|---|
| —CH(C₂H₅)₂ | 3 | 8 | 4 | 6 | 0 | 0 | 9 | 9 | 8 | 6 | 2 | 0 | 0 | 1 |
|  | 1 | 8 | 0 | 0 | 0 | 0 | 9 | 9 | 8 | 1 | 0 | 0 | 0 | 1 |

TABLE VII

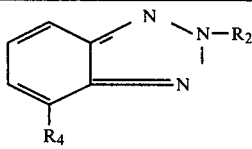

PREEMERGENCE HERBICIDAL ACTIVITY OF 2H-BENZOTRIAZOLES HAVING THE ABOVE STRUCTURE

| STRUCTURE R₂ | R₄ | RATE LBS./ACRE | LA | MU | PI | RW | MG | BA | CR | FO | WO | CN | CO | SY | RI |
|---|---|---|---|---|---|---|---|---|---|---|---|---|---|---|---|
| —CH(CH₃)₂ | NO₂ | 4 | 5 | 7 | 9 | 0 | 0 | 3 | 8 | 5 | 0 | 0 | 5 | 3 | 9 |
|  |  | 1 | 0 | 5 | 8 | 0 | 0 | 0 | 2 | 2 | 0 | 0 | 0 | 3 | 1 |
| —CH(C₂H₅)₂ | NO₂ | 4 | 9 | 9 | 9 | 0 | 0 | 9 | 9 | 9 | 7 | 0 | 0 | 0 | 9 |
|  |  | 1 | 0 | 0 | 2 | 0 | 0 | 6 | 7 | 4 | 0 | 0 | 0 | 0 | 0 |
| 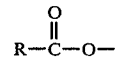 | NO₂ | 4 | 9 | 9 | 9 | 0 | 1 | 6 | 9 | 7 | 1 | 3 | 7 | 2 | 1 |
|  |  | 1 | 0 | 5 | 9 | 0 | 0 | 3 | 2 | 1 | 0 | 2 | 7 | 1 | 1 |
| 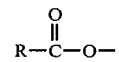 | NO₂ | 4 | 3 | 7 | 5 | 5 | 0 | 6 | 6 | 6 | 0 | 0 | 0 | 0 | 2 |

We claim:

1. A method for the control of undesirable plant species comprising; applying to undesirable plants or soil containing seeds, a herbicidally effective amount of a compound having the formula:

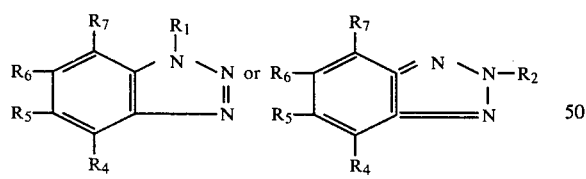

wherein R₁ is secondary alkyl C₃–C₇; benzyl; cyclohexenyl; alkoxy C₃–C₄; acetyl; chloroacetyl; 2-butan-3-one; isobutyryl; t-butyl; methoxymethylpropyl; 2-cyclohexyl-1-one;

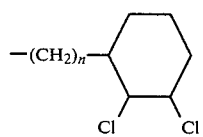

where n is 0 or 1; or —(CH₂)ₙ-cycloalkyl C₃–C₈ optionally substituted with hydroxy, alkoxy C₁–C₃, alkyl C₁–C₃, or $$R-\overset{O}{\underset{\|}{C}}-O-$$

where R is hydrogen or C₁–C₂ alkyl and n is 0 or 1;

R₂ is secondary alkyl C₃–C₇; benzyl; cycloalkenyl C₃–C₈; —(CH₂)ₙ-cycloalkyl (C₃–C₈) optionally substituted with hydroxy, alkoxy C₁–C₃, alkyl C₁–C₃ or $$R-\overset{O}{\underset{\|}{C}}-O-$$

where R is hydrogen or C₁–C₂ alkyl and n is 0 or 1; 2-cyclohexyl-1-one or

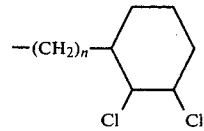

where n is 0 or 1;

R₄ represents, chloro, isothiacyano, cyano, methoxy or nitro; R₅ and R₆ and R₇ are each hydrogen wherein said compound is applied at the rate of from about 0.25 lb./acre to about 4.0 lbs./acre.

2. A method according to claim 1 for the postemergence control of undesirable plants, wherein the compound is applied to the foliage of the undesirable plants.

3. A method according to claim 1 for the preemergence control of undesirable plants, wherein the compound is applied to soil containing seeds of the undesirable plants.

4. A method according to claim 1 wherein $R_1$ represents secondary alkyl $C_3$–$C_7$; benzyl; cyclohexenyl; —$(CH_2)_n$-cycloalkyl $(C_3$–$C_8)$ optionally substituted with a hydroxy, alkoxy $C_1$–$C_3$, alkyl $C_1$–$C_3$, or

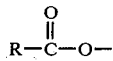

wherein R is hydrogen or $C_1$–$C_2$ alkyl and n is 0 or 1; 2-cyclohexyl-1-one or

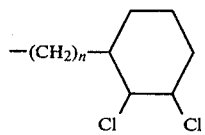

where n is 0 or 1; $R_4$ represents, chloro, isothiocyano, cyano, methoxy or nitro.

5. A method according to claim 1, wherein $R_2$ represents secondary alkyl $C_3$–$C_7$; benzyl; cyclohexenyl —$(CH_2)_n$-cycloalkyl $(C_3$–$C_8)$ optionally substituted with hydroxy, alkoxy $C_1$–$C_3$, alkyl $C_1$–$C_3$ or

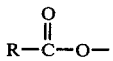

wherein R is hydrogen $C_1$–$C_2$ alkyl and n is 0 or 1; 2-cyclohexyl-b 1-one or

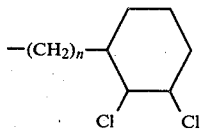

where n is 0 or 1; $R_4$ represents, chloro, isothiocyano, cyano, methoxy or nitro.

6. A method according to claim 1 wherein $R_1$ is acetyl; chloroacetyl; 2-butanone; methoxymethylpropyl; isobutyryl or tertiarybutyl and $R_4$, $R_5$, $R_6$ and $R_7$ are as described in said claim 1.

7. A method according to claim 2 wherein $R_1$ is secondary alkyl $C_3$–$C_7$; —$(CH_2)_n$-cycloalkyl $(C_3$–$C_8)$ optionally substituted with a hydroxy, alkoxy $C_1$–$C_3$, alkyl $C_1$–$C_3$ or

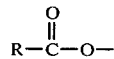

wherein R is hydrogen or $C_1$–$C_2$ alkyl and n is 0 or 1; 2-cyclohexyl-1-one or

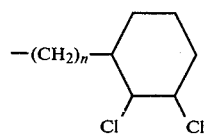

where n is 0 or 1.

8. A method according to claim 2 wherein the compound is 1-benzyl-4-nitro-1-$\underline{H}$-benzotriazole.

9. A method according to claim 2 wherein the compound is 1-isopropyl-4-nitro-1-$\underline{H}$-benzotriazole.

10. A method according to claim 2 wherein the compound is 1-(2,3-dichlorocyclohexyl)-4-nitro-1-$\underline{H}$-benzotriazole.

11. A method for the control of undesirable plant species according to claim 1 wherein the compound is 1-cyclohexyl-4-nitro-1$\underline{H}$-benzotriazole.

12. A method of the control of undesirable plant species according to claim 1 wherein the compound is 1-(2-methylcyclohexyl)-4-nitro-1$\underline{H}$-benzotriazole.

13. A method for the control of undesirable plant species according to claim 1 wherein the compound is 1-(2-cyclohexen-1-yl)-4-nitro-1$\underline{H}$-benzotriazole.

14. A method for the control of undesirable plant species according to claim 1 wherein the compound is 1-cyclohexyl-4-cyano-1$\underline{H}$-benzotriazole.

15. A method for the control of undesirable plant species according to claim 1 wherein the compound is 1-cyclohexyl-4-chloro-1$\underline{H}$-benzotriazole.

* * * * *